(12) United States Patent
Kalkum et al.

(10) Patent No.: US 8,449,894 B2
(45) Date of Patent: May 28, 2013

(54) *ASPERGILLUS* VACCINE PREPARATION AND METHODS OF MAKING AND USING THEREOF

(75) Inventors: Markus Kalkum, Azusa, CA (US); Diana Diaz-Arevalo, Monrovia, CA (US); James I. Ito, La Verne, CA (US); Joseph M. Lyons, Claremont, CA (US); Teresa B. Hong, El Monte, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 11/754,252

(22) Filed: May 25, 2007

(65) Prior Publication Data

US 2008/0085286 A1    Apr. 10, 2008

Related U.S. Application Data

(60) Provisional application No. 60/809,104, filed on May 26, 2006.

(51) Int. Cl.
| | |
|---|---|
| *A61K 39/00* | (2006.01) |
| *C07K 1/00* | (2006.01) |
| *C07K 14/00* | (2006.01) |
| *C07K 17/00* | (2006.01) |

(52) U.S. Cl.
USPC .................. 424/274.1; 424/184.1; 424/185.1; 530/350

(58) Field of Classification Search
None
See application file for complete search history.

(56) References Cited

U.S. PATENT DOCUMENTS

| | | | | |
|---|---|---|---|---|
| 6,248,329 | B1 * | 6/2001 | Chandrashekar et al. | 424/191.1 |
| 6,800,290 | B2 * | 10/2004 | Sturaro et al. | 424/275.1 |
| 2005/0281816 | A1 * | 12/2005 | Lamping et al. | 424/144.1 |

FOREIGN PATENT DOCUMENTS

WO    WO 02/093998 A2 * 11/2002

OTHER PUBLICATIONS

Ramaiah et al(Indian Journal of Marine Sciences, 35:380-387, 2006.*
Encyclopedia Britannica: Fungal Diseases of Plants. http://www.britannica.com/eb/article-9115892/Table-16-Some-Fungal-Diseases-of-Plants Retrieved online Apr. 16, 2008.*
Mechanisms of Microbial Disease (Moselio et al (eds) 3$^{rd}$ edititon 1999 p. 419-439.*
Samson, R. In *Aspergilllus fumigatus*, Contrib Microbiol. Brakhage et al (eds) Basel, Karger, 1999, vol. 2, p. 5-20.*
Deepe et al Expert Rev. Vaccines 3:701-709, 2004.*
Sequence search results—2 pages.*
Definition of "particulate." Merriam-Webster Online Dictionary. 2008. Merriam-Webster Online. Dec. 29, 2008 http://www.merriam-webster.com/dictionary/particulate.*
Definition of "particle." Merriam-Webster Online Dictionary. 2008. Merriam-Webster Online. Dec. 29, 2008 http://www.merriam-webster.com/dictionary/particle.*
Ellis, R.W. (Chapter 29 of "Vaccines" [Plotkin, S.A. et al. (eds) published by W. B. Saunders company (Philadelphia) in 1988.*
Definition of "Vaccine"—The Dictionary of Immunology, Herbert et al eds, Academic Press, 1995.*
Kersten et al. Novel Vaccination Strategies, Edited by Stefan H Kaufmann. 2004 Wiley-VCH Verlag GmBH & Co. Chapter 9 p. 173-196.*
O'Hagan et al. Novel Vaccination Strategies, Edited by Stefan H Kaufmann. 2004 Wiley-VCH Verlag GmBH & Co. Chapter 8 p. 147-172.*
Houghten et al. (New Approaches to Immunization, Vaccines 86, Cold Spring Harbor Laboratory, p. 21-25, 1986).*
Colman et al. (Research in Immunology 145: 33-36, 1994.*
Wilson et al Bioscience Reports, vol. 22, No. 2, p. 309-322, Apr. 2002.*
UniprotKB/Swiss-Prot accession # O43099, 1998—amino acid sequence of *Aspergillus fumigatus* Asp f 3.*
Kesik et al. Immunology Letters 91 (2004) 197-204.*
Newman et al. Vaccine Adjuvants. Exp. Opin. Ther. Patents (2000) 10(3):279-314.*
Ferreira et al. In Advances in Immunology, vol. 84, Elsevier Academic Press, 2004, p. 84-85 and 96-97.*
Bozza, S., et al. 2002. Vaccination of mice against invasive aspergillosis with recombinant *Aspergillus* proteins and CpG oligodeoxynucleotides as adjuvants. Microbes Infect 4:1281-1290.
Bozza, S., et al. 2004. Dendritic cell-based vaccination against opportunistic fungi. Vaccine 22:857-864.
Bozza, S., et al. 2003. A dendritic cell vaccine against invasive aspergillosis in allogeneic hematopoietic transplantation. Blood 102:3807-3814.
Hemmann, S., Blaser, K., Crameri, R. 1997. Allergens of *Aspergillus fumigatus* and *Candida boidinii* share IgE-binding epitopes. Am J Respir Crit Care Med 156:1956-1962.
Ito, J. I., and J. M. Lyons. 2002. Vaccination of corticosteroid immunosuppressed mice against invasive pulmonary aspergillosis. J Infect Dis 186:869-871.
Kurup, V. P., et al. 2001. Purified recombinant *A. fumigatus* allergens induce different responses in mice. Clin Immunol 98:327-336.
Latge, J. P. 1999. Antigen and DNA patterns characteristic of *Aspergillus fumigatus*. Contrib Microbiol 2:69-87.
Latge, J. P. 1999. *Aspergillus fumigatus* and aspergillosis. Clin Microbiol Rev 12:310-350.
Nierman, W. C., et al al. 2005. Genomic sequence of the pathogenic and allergenic filamentous fungus *Aspergillus fumigatus*. Nature 438:1151-1156.
Ramachandran, H., et al. 2002. IgE binding conformational epitopes of Asp f 3, a major allergen of *Aspergillus fumigatus*. Clin Immunol 103:324-333.
Rementeria, A., et al. 2005. Genes and molecules involved in *Aspergillus fumigatus* virulence. Rev Iberoam Micol 22:1-23.

* cited by examiner

*Primary Examiner* — Oluwatosin Ogunbiyi

(74) *Attorney, Agent, or Firm* — Perkins Coie LLP; Patrick D. Morris

(57) ABSTRACT

The present invention relates to compositions and methods in preventing and/or treating diseases caused by *Aspergillus*. In particular, the present invention is directed to *Aspergillus* vaccine preparations and methods of making and using thereof.

1 Claim, 19 Drawing Sheets

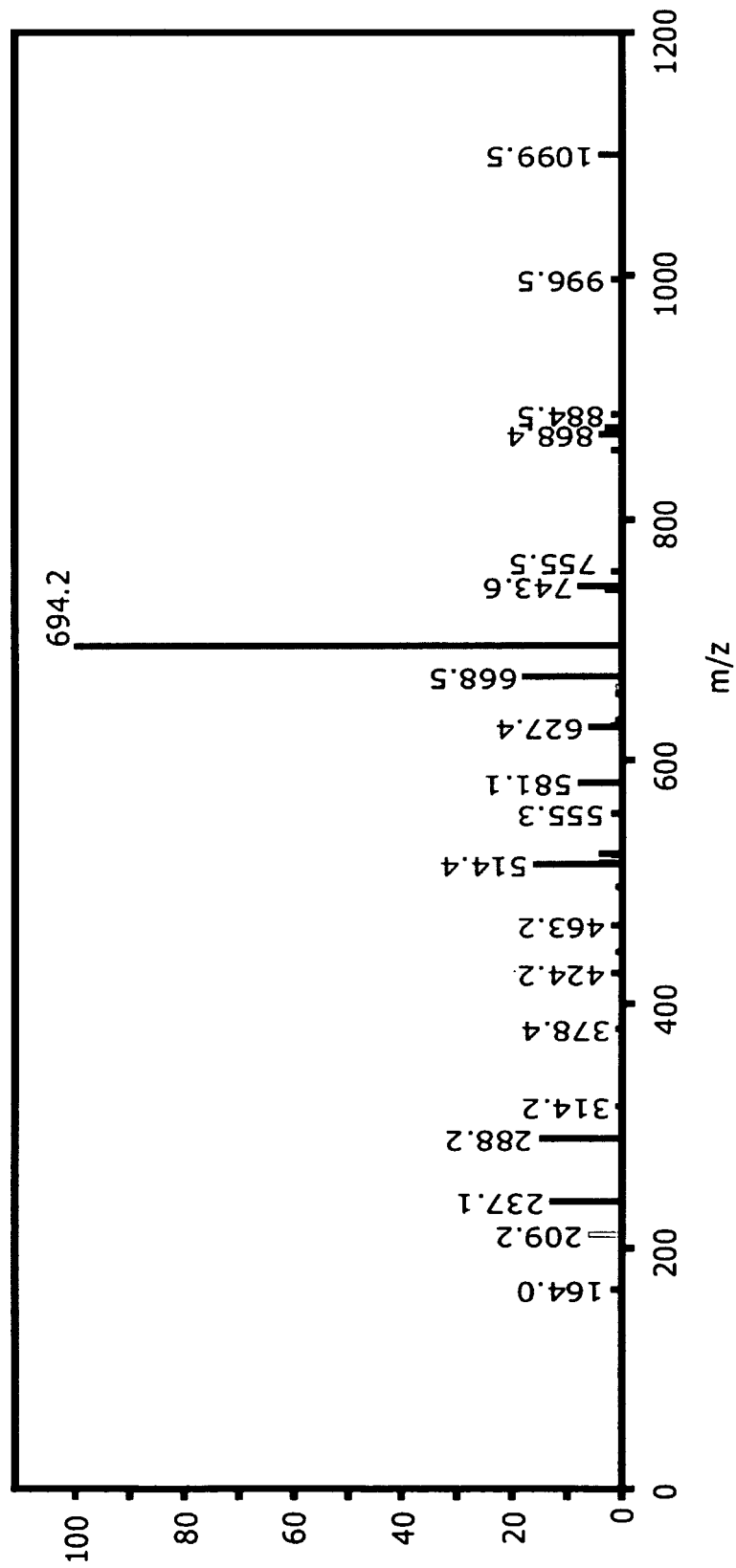
Figure 9 (con't.)

SEQUENCE LISTING

```
<160> NUMBER OF SEQ ID NOS: 11

<210> SEQ ID NO 1
<211> LENGTH: 31
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (1)..(6)
<223> OTHER INFORMATION: SacI site

<400> SEQUENCE: 1
gagctcatgt ctggactcaa ggccggtgac a                              31

<210> SEQ ID NO 2
<211> LENGTH: 31
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (1)..(6)
```

```
<400> SEQUENCE: 2
ggtaccttac aggtgcttga ggacggtctc g                                    31

<210> SEQ ID NO 3
<211> LENGTH: 24
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (1)..(6)
<223> OTHER INFORMATION: StuI site

<400> SEQUENCE: 3
aggcctgtct tctcttacat cccc                                            24

<210> SEQ ID NO 4
<211> LENGTH: 25
<212> TYPE: DNA
<213> ORGANISM: Artificial
<220> FEATURE:
<223> OTHER INFORMATION: PCR primer

<400> SEQUENCE: 4
attgaccacg gctagattac ctacg                                           25

<210> SEQ ID NO 5
<211> LENGTH: 25
<212> TYPE: DNA
<213> ORGANISM: Artificial
<220> FEATURE:
<223> OTHER INFORMATION: PCR primer

<400> SEQUENCE: 5
cgtaggtaat ctagccgtgg tcaat                                           25

<210> SEQ ID NO 6
<211> LENGTH: 168
<212> TYPE: PRT
<213> ORGANISM: Aspergillus fumigatus

<400> SEQUENCE: 6

Met Ser Gly Leu Lys Ala Gly Asp Ser Phe Pro Ser Asp Val Val Phe
1               5                   10                  15

Ser Tyr Ile Pro Trp Ser Glu Asp Lys Gly Glu Ile Thr Ala Cys Gly
            20                  25                  30

Ile Pro Ile Asn Tyr Asn Ala Ser Lys Glu Trp Ala Asp Lys Lys Val
        35                  40                  45

Ile Leu Phe Ala Leu Pro Gly Ala Phe Thr Pro Val Cys Ser Ala Arg
    50                  55                  60

His Val Pro Glu Tyr Ile Glu Lys Leu Pro Glu Ile Arg Ala Lys Gly
65                  70                  75                  80

Val Asp Val Val Ala Val Leu Ala Tyr Asn Asp Ala Tyr Val Met Ser
                85                  90                  95

Ala Trp Gly Lys Ala Asn Gln Val Thr Gly Asp Asp Ile Leu Phe Leu
            100                 105                 110

Ser Asp Pro Asp Ala Arg Phe Ser Lys Ser Ile Gly Trp Ala Asp Glu
        115                 120                 125

Glu Gly Arg Thr Lys Arg Tyr Ala Leu Val Ile Asp His Gly Lys Ile
    130                 135                 140
```

Thr Tyr Ala Ala Leu Glu Pro Ala Lys Asn His Leu Glu Phe Ser Ser
145                 150                 155                 160

Ala Glu Thr Val Leu Lys His Leu
                165

<210> SEQ ID NO 7
<211> LENGTH: 200
<212> TYPE: PRT
<213> ORGANISM: Artificial
<220> FEATURE:
<223> OTHER INFORMATION: Recombinant His-tagged Aspergillus fumigatus
      Asp f 3
<220> FEATURE:
<221> NAME/KEY: MISC_FEATURE
<222> LOCATION: (1)..(32)

<400> SEQUENCE: 7

Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Met Ser Gly Leu Lys Ala Gly Asp Ser Phe Pro Ser Asp Val Val Phe
        35                  40                  45

Ser Tyr Ile Pro Trp Ser Glu Asp Lys Gly Glu Ile Thr Ala Cys Gly
    50                  55                  60

Ile Pro Ile Asn Tyr Asn Ala Ser Lys Glu Trp Ala Asp Lys Lys Val
65                  70                  75                  80

Ile Leu Phe Ala Leu Pro Gly Ala Phe Thr Pro Val Cys Ser Ala Arg
                85                  90                  95

His Val Pro Glu Tyr Ile Glu Lys Leu Pro Glu Ile Arg Ala Lys Gly
            100                 105                 110

Val Asp Val Val Ala Val Leu Ala Tyr Asn Asp Ala Tyr Val Met Ser
        115                 120                 125

Ala Trp Gly Lys Ala Asn Gln Val Thr Gly Asp Ile Leu Phe Leu
    130                 135                 140

Ser Asp Pro Asp Ala Arg Phe Ser Lys Ser Ile Gly Trp Ala Asp Glu
145                 150                 155                 160

Glu Gly Arg Thr Lys Arg Tyr Ala Leu Val Ile Asp His Gly Lys Ile
                165                 170                 175

Thr Tyr Ala Ala Leu Glu Pro Ala Lys Asn His Leu Glu Phe Ser Ser
            180                 185                 190

Ala Glu Thr Val Leu Lys His Leu
        195                 200

<210> SEQ ID NO 8
<211> LENGTH: 176
<212> TYPE: PRT
<213> ORGANISM: Artificial
<220> FEATURE:
<223> OTHER INFORMATION: Recombinant His-tagged N-terminal truncated
      Aspergillus fumigatus Asp f 3
<220> FEATURE:
<221> NAME/KEY: MISC_FEATURE
<222> LOCATION: (1)..(22)

<400> SEQUENCE: 8

Met Arg Gly Ser His His His His His His Gly Ser Gly Ser Gly Ser
1               5                   10                  15

Gly Ile Glu Gly Arg Pro Val Phe Ser Tyr Ile Pro Trp Ser Glu Asp
            20                  25                  30

Lys Gly Glu Ile Thr Ala Cys Gly Ile Pro Ile Asn Tyr Asn Ala Ser

```
                    35                  40                  45
Lys Glu Trp Ala Asp Lys Val Ile Leu Phe Ala Leu Pro Gly Ala
 50                  55                  60

Phe Thr Pro Val Cys Ser Ala Arg His Val Pro Glu Tyr Ile Glu Lys
 65                  70                  75                  80

Leu Pro Glu Ile Arg Ala Lys Gly Val Asp Val Val Ala Val Leu Ala
                     85                  90                  95

Tyr Asn Asp Ala Tyr Val Met Ser Ala Trp Gly Lys Ala Asn Gln Val
                    100                 105                 110

Thr Gly Asp Asp Ile Leu Phe Leu Ser Asp Pro Asp Ala Arg Phe Ser
                115                 120                 125

Lys Ser Ile Gly Trp Ala Asp Glu Glu Gly Arg Thr Lys Arg Tyr Ala
130                 135                 140

Leu Val Ile Asp His Gly Lys Ile Thr Tyr Ala Ala Leu Glu Pro Ala
145                 150                 155                 160

Lys Asn His Leu Glu Phe Ser Ser Ala Glu Thr Val Leu Lys His Leu
                165                 170                 175

<210> SEQ ID NO 9
<211> LENGTH: 174
<212> TYPE: PRT
<213> ORGANISM: Artificial
<220> FEATURE:
<223> OTHER INFORMATION: Recombinant His-tagged C-terminal truncated
      Aspergillus fumigatus Asp f 3
<220> FEATURE:
<221> NAME/KEY: MISC_FEATURE
<222> LOCATION: (1)..(32)
<223> OTHER INFORMATION: His tag

<400> SEQUENCE: 9

Met Arg Gly Ser His His His His Gly Ser Gly Ser Gly Ser
 1               5                  10                  15

Gly Ile Glu Gly Arg Pro Tyr Asn Gly Thr Gly Ser Ala Cys Glu Leu
                 20                  25                  30

Met Ser Gly Leu Lys Ala Gly Asp Ser Phe Pro Ser Asp Val Val Phe
             35                  40                  45

Ser Tyr Ile Pro Trp Ser Glu Asp Lys Gly Glu Ile Thr Ala Cys Gly
 50                  55                  60

Ile Pro Ile Asn Tyr Asn Ala Ser Lys Glu Trp Ala Asp Lys Lys Val
 65                  70                  75                  80

Ile Leu Phe Ala Leu Pro Gly Ala Phe Thr Pro Val Cys Ser Ala Arg
                 85                  90                  95

His Val Pro Glu Tyr Ile Glu Lys Leu Pro Glu Ile Arg Ala Lys Gly
                100                 105                 110

Val Asp Val Val Ala Val Leu Ala Tyr Asn Asp Ala Tyr Val Met Ser
            115                 120                 125

Ala Trp Gly Lys Ala Asn Gln Val Thr Gly Asp Asp Ile Leu Phe Leu
        130                 135                 140

Ser Asp Pro Asp Ala Arg Phe Ser Lys Ser Ile Gly Trp Ala Asp Glu
145                 150                 155                 160

Glu Gly Arg Thr Lys Arg Tyr Ala Leu Val Ile Asp His Gly
                165                 170

<210> SEQ ID NO 10
<211> LENGTH: 150
<212> TYPE: PRT
<213> ORGANISM: Artificial
<220> FEATURE:
```

-continued

```
<223> OTHER INFORMATION: Recombinant His-tagged N- and C-terminal
      truncated Aspergillus fumigatus Asp f 3
<220> FEATURE:
<221> NAME/KEY: MISC_FEATURE
<222> LOCATION: (1)..(22)

<400> SEQUENCE: 10

Met Arg Gly Ser His His His His His His Gly Ser Gly Ser Gly Ser
1               5                   10                  15

Gly Ile Glu Gly Arg Pro Val Phe Ser Tyr Ile Pro Trp Ser Glu Asp
                20                  25                  30

Lys Gly Glu Ile Thr Ala Cys Gly Ile Pro Ile Asn Tyr Asn Ala Ser
            35                  40                  45

Lys Glu Trp Ala Asp Lys Lys Val Ile Leu Phe Ala Leu Pro Gly Ala
    50                  55                  60

Phe Thr Pro Val Cys Ser Ala Arg His Val Pro Glu Tyr Ile Glu Lys
65                  70                  75                  80

Leu Pro Glu Ile Arg Ala Lys Gly Val Asp Val Val Ala Val Leu Ala
                85                  90                  95

Tyr Asn Asp Ala Tyr Val Met Ser Ala Trp Gly Lys Ala Asn Gln Val
                100                 105                 110

Thr Gly Asp Asp Ile Leu Phe Leu Ser Asp Pro Asp Ala Arg Phe Ser
            115                 120                 125

Lys Ser Ile Gly Trp Ala Asp Glu Glu Gly Arg Thr Lys Arg Tyr Ala
    130                 135                 140

Leu Val Ile Asp His Gly
145                 150

<210> SEQ ID NO 11
<211> LENGTH: 8
<212> TYPE: PRT
<213> ORGANISM: Aspergillus fumigatus

<400> SEQUENCE: 11

Lys Glu Asp Val Ala Glu Ala Val
1               5
```

ASPERGILLUS VACCINE PREPARATION AND METHODS OF MAKING AND USING THEREOF

REFERENCE TO RELATED APPLICATIONS

The present utility application claims priority to U.S. Provisional Patent Application No. 60/809,104, filed May 26, 2006, the disclosure of which is incorporated by reference herein in its entirety.

BACKGROUND

Invasive pulmonary aspergillosis (IPA) is a rapidly progressive and oftentimes fatal disease common among severely immunocompromised individuals, including patients with hematologic malignancies, neutropenia, chronic granulomatous disease, solid organ transplants (SOT), allogeneic hematopoietic cell transplants (HCT), AIDS, or major burns. Despite the development and use of new antifungal agents and the implementation of antifungal prophylaxis, the incidence and mortality rates remain high (Lin 2001).

IPA is most frequently observed in SOT and HCT recipients following the prolonged immunosuppression required to avoid graft rejection (Duthie 1995; Denning 1998; Maschke 1999; Ho 2000; Baddley 2001; Subira 2002; Kibbler 2003; Wiederhold 2003). The ubiquitous mold *Aspergillus fumigatus* is the most frequently isolated causative agent of IPA (Latge 1999a). *A. fumigatus* is also involved in allergic bronchopulmonary aspergillosis (ABPA) and other fungal diseases.

Healthy individuals rarely contract respiratory fungal infections, being protected against inhaled spores (conidia) through innate immunity provided by alveolar macrophages and neutrophils (Schaffner 1982). Opsonizing antibodies have been suggested to play a role in enhancing phagocytosis of conidia and in B-cell mediated memory immunity (Montagnoli 2003). The immunosuppressive effects of corticosteroids are thought to be due to suppression of the antimicrobial activity of macrophages and neutrophils (Schaffner 1985; Roilides 1993a). Although cytokines such as granulocyte-macrophage colony-stimulating factor (GM-CSF) and interferon gamma (IFN-γ) prevent corticosteroid-induced immunosuppression in vitro (Roilides 1993a; Roilides 1993b), use of these cytokines has not been shown to restore immunocompetence or to prevent or enhance therapy of invasive aspergillosis (Casadevall 2001).

Currently available antifungal agents have had only limited success in treating IPA (Ho 2000) and are also associated with serious toxicities such as nephrotoxicity and hepatotoxicity (Ho 2000; Gupta 2003; Hamza 2004). Therefore, there is a need for new antifungal agents that prevent and treat IPA and other diseases caused by *Aspergillus* with minimal toxicity.

SUMMARY

In certain embodiments, a composition is provided for preventing a disease caused by a fungal pathogen comprising the *Aspergillus fumigatus* protein Asp f 3. In certain of these embodiments, the Asp f 3 protein is recombinant. In certain of these embodiments, the recombinant protein is full-length Asp f 3, comprising residues 1 to 168. In certain embodiments, the recombinant protein comprises residues 15 to 168, 1 to 142, or 15 to 142 of SEQ ID NO:6. In certain embodiments, the recombinant protein comprises residues 54 to 64 or 65 to 77 of SEQ ID NO:6. In certain embodiments, the recombinant protein is in particulate form. In certain embodiments, the disease prevented by the composition is invasive pulmonary aspergillosis, *aspergillus* tracheobronchitis, invasive *aspergillus* sinusitis, disseminated aspergillosis, cutaneous aspergillosis, and cerebral aspergillosis.

In certain embodiments, a method is provided for preventing a disease caused by a fungal pathogen in a subject comprising administering a composition comprising the *Aspergillus fumigatus* protein Asp f 3. In certain of these embodiments, the Asp f 3 protein is recombinant. In certain of these embodiments, the recombinant protein is full-length Asp f 3, comprising residues 1 to 168. In certain embodiments, the recombinant protein comprises residues 15 to 168, 1 to 142, or 15 to 142 of SEQ ID NO:6. In certain embodiments, the recombinant protein comprises residues 54 to 64 or 65 to 77 of SEQ ID NO:6. In certain embodiments, the recombinant protein is in particulate form. In certain embodiments, the disease prevented by the composition is invasive pulmonary aspergillosis, *aspergillus* tracheobronchitis, invasive *aspergillus* sinusitis, disseminated aspergillosis, cutaneous aspergillosis, and cerebral aspergillosis.

DETAILED DESCRIPTION

Figure 1:
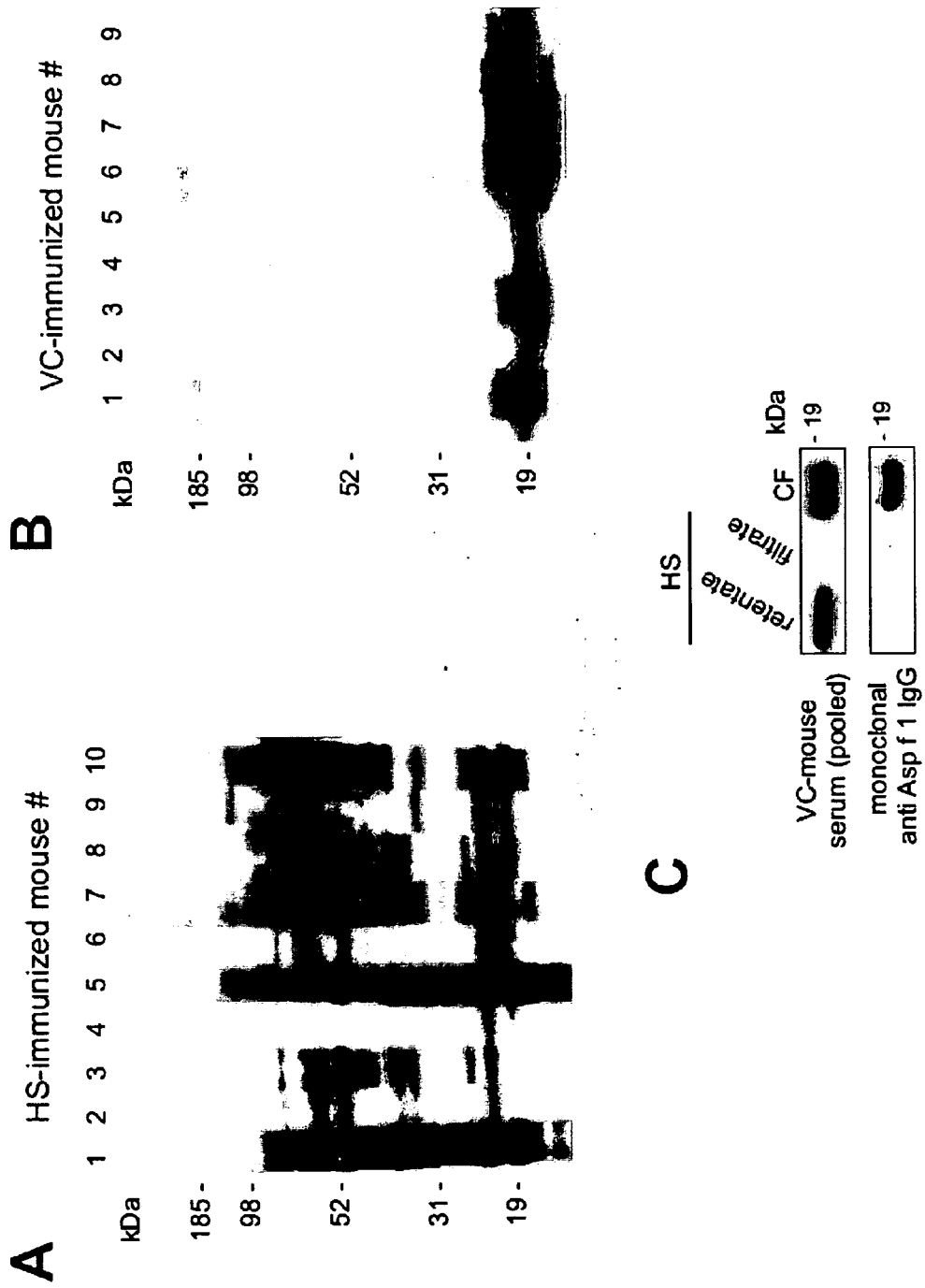
FIG. 1: Western blots of hyphal protein extracts developed with sera from individual mice after immunization with either (A) hyphal sonicate (HS) or (B) through non-lethal infection with viable conidia (VC). Goat anti-mouse IgG-HRP conjugate was used for chemiluminescent detection. Both vaccination methods are highly protective (Ito 2002) but differ significantly in their immunoglobulin response regarding antigen-specificity as well as animal-to-animal variation. (C) Western blots of pre-fractionated HS and culture filtrate (CF). HS has passed through a 30-kDa MWCO membrane and was then separated into filtrate and retentate using a 10-kDa MWCO membrane.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Abbreviations

ABPA, allergic bronchopulmonary aspergillosis; CF, culture filtrate; HCT, allogeneic hematopoietic cell transplants; HE, hematoxylin-and-eosin; HS, hyphal sonicate; IPA, invasive pulmonary aspergillosis; MWCO, molecular weight cutoff; PBS, phosphate buffered saline; PMN, polymorphonuclear leukocytes; SOT, solid organ transplants; TM, TITERMAX®; VC, viable conidia.

The restoration of the immune system is the key challenge for hematopoietic cell transplant recipients in which immunopathologic effects, namely graft-versus-host disease, need to be suppressed. It has been shown previously that mice vaccinated subcutaneously with crude fungal protein extracts or by intranasal inoculation of viable conidia survive an (otherwise) lethal pulmonary challenge under corticosteroid immunosuppression (Ito 2002). Although crude protein mixtures or deliberate exposure to *aspergillus* would not be suitable for use in humans due to safety concerns related to toxicity and allergenicity, the use of a recombinant protein-vaccine is both attractive and feasible. Such a vaccine could be produced in large amounts at low costs and with straight-forward quality and safety controls designed to avoid allergenicity.

Defined by IgE binding, about 58 allergens from *A. fumigatus* have thus far been characterized and at least nine additional allergens have been predicted based on similarity with other fungal allergens (Latge 1999a; Latge 1999b; Ramachandran 2003; Nierman 2005; Rementeria 2005). Although most allergens react with IgE antibodies from ABPA patients, it has not been clear whether subcutaneous injections with purified forms of such allergens would actually hypersensitize non-allergic individuals. In fact, it has been shown that total murine IgE production induced through repeated pulmonary exposure to recombinant allergens, including Asp f 3, only reached levels that were 20% or less than those obtained through exposure to crude *A. fumigatus* extracts (Kurup 2001).

In the present disclosure, an immunochemical and mass spectrometric approach has been utilized to identify the dominant antigen to which antibodies are produced in naïve immunocompetent mice following naso-pulmonary exposure to viable *A. fumigatus* conidia, as previously described (Ito 2002). Mice protectively immunized in this manner elicit a specific IgG2a response against allergen Asp f 3, which is consistent with a $T_H1$ type response. Subcutaneous injection of various versions of recombinant Asp f 3 (rAsp f 3), with or without deletion of the "allergenic" IgE-binding epitope, provides a significant degree of protection in corticosteroid immunosuppressed mice. Transfer of the resultant rAsp f 3 IgG antibodies to non-immunized mice does not confer protection, suggesting that Asp f 3 protects via a cell-based mechanism.

A novel mass spectrometry-based method for identifying vaccine candidates that function via T cell-based mechanisms was utilized to identify T and B cell epitopes in rAsp f 3. A series of rAsp f 3 peptides were generated by trypsin, Lys-C, and pepsin digestion, and these peptides were analyzed by MALDI-Q-TOF, MALDI-ion trap, and LC/FTICR-MS. The ability of the peptides to induce a proliferative response of splenocytes from rAsp f3 immunized mice was also measured. Using this method, both T and B cell epitopes from rAsp f 3 were identified. The tryptic peptides induced a proliferative response that was comparable to either rAsp f 3 or rAsp f 3 variants, suggesting that proteolysis did not destroy the dominant T cell epitope(s). Employing the same method using digested peptides from *A. fumigatus* hyphal protein extracts, an additional T cell epitope was identified in the protein NAD-dependent formate dehydrogenase. This method provides a valuable tool for identifying vaccine candidates that may be used to protect an immunosuppressed subject against invasive aspergillosis through a T cell-based mechanism.

Bozza et al. previously demonstrated a protective effect for the recombinant *A. fumigatus* allergen Asp f 16, but did not find Asp f 3 to be protective following intranasal vaccination in the presence of CpG oligodeoxynucleotides (ODNS) as adjuvants (Bozza 2002). However, the approach of Bozza et al. differed substantially from that set forth herein. The routes of vaccination (subcutaneous vs. intranasal, TM adjuvant or particulate form vs. ODNs) and the animal models used differ significantly. The present disclosure utilizes a corticosteroid immunosuppression model, whereas Bozza et al. used a cyclophosphamide-induced neutropenic model. The purpose of using the corticosteroid-induced immunosuppression model was to simulate the effects of prolonged immunosuppression that recipients of hematopoietic cell transplants experience to control GvHD. Such prolonged corticosteroid immunosuppression is the number one risk factor for invasive fungal infections.

Orsborn et al. have recently shown that vaccinations with recombinant Pmp 1 can protect mice against *Coccidioides posadasii* infections. Asp f 3 is a homologue to Pmp 1 from *C. posadasii*, with which it shares ~68% sequence identity. Both proteins have some sequence homology with two presumed peroxisomal matrix proteins, PMP20 (PMPA and PMPB), from *Candida boidinii* (Garrard 1989) with which Asp f 3 was reported to share a common IgE-binding epitope (Hemmann 1997). Several genes of other fungi encode sequences that are nearly identical to *A. fumigatus* Asp f 3. These include PMP20, Asp f 3 from *Aspergillus nidulans* FGSC A4 (accession # AN8692.2) (90% identity), a cDNA from *Aspergillus oryzae* RIB40 (accession # AN8692.2) (86% identity), Pen c 3 from *Penicillium citrinum* (accession # AF144753) 81% identity), and others with significant similarity such as a peroxisomal-like protein mRNA sequence from *Paracoccidioides brasiliensis* (accession # AY376436) (67% identity) and a putative alkyl hydroperoxide reductase from *Candida albicans* SC5314 (accession # XM_715419) (38% identity). The Asp f 3-based vaccine disclosed herein may therefore provide cross-protection against various fungal pathogens. In certain embodiments, the vaccines disclosed herein prevent a disease caused by a fungal pathogen belonging to the genus *Aspergillus*, such as for example *Aspergillus fumigatus* or *Aspergillus nidulans*. Further, in certain embodiments the vaccines disclosed herein prevent a disease caused by a fungal pathogen that expresses a protein having at least 70% identity to *Aspergillus fumigatus* Asp f 3.

The four recombinant versions of rAsp f 3 tested herein appear to be processed differently during immunization. It should also be noted that both full-length rAsp f 3 (1-168) and double truncated rAsp f 3 (15-142) could be purified from *E. coli* lysates in the absence of urea. In contrast, the N- and C-terminal truncations comprising residues 15-168 and 1-142, respectively, are not very soluble and needed to be purified from the lysates with urea. These findings suggest distinct structural properties for the various versions of rAsp f 3. Such conformational differences could influence phagocytosis, proteosomal processing and MHC display, and thus may result in different immunogenic properties. This is supported by the protective effect of the adjuvant-free particulate rAsp f 3 compared to the lack of protection observed with soluble adjuvant-free rAsp f 3. The use of particulate vaccines is the basis for various immunization strategies, including the use of alum and emulsions as particle forming matrix for soluble vaccine candidates. In this context, particulate recombinant vaccines against hepatitis viruses have been produced and immunogenic differences between particulate and non-particulate antigens have been found (Li 2005; Huang 2006).

The compositions provided herein may comprise recombinant Asp f 3 or fragments thereof. In certain of these embodiments, the Asp f 3 protein or fragment there may include a label or tag, such as for example a His tag. By "fragments thereof" is meant any fragment of the Asp f 3 sequence set forth in SEQ ID NO:6 that retains the ability to provide protection in a subject against a disease caused by a fungal pathogen. In certain embodiments, this fragment may be an N-terminal, C-terminal, or N/C-terminal truncations. In certain of these embodiments, the truncation may be a deletion of five amino acids from the N- or C-terminal end of Asp f 3 or both. In certain other embodiments, the truncation may be 10, 15, 20, 25, 30, 35, 40, 45, or 50 amino acids. In certain embodiments, a truncated recombinant Asp f 3 of the present invention may have the sequence set forth in any of SEQ ID NOs: 8-10.

The compositions provided herein may be administered to an immunocompromised subject to prevent a disease caused by a fungal pathogen. This immunocompromise may arise from hematologic malignancies, neutropenia, chronic granulomatous disease, AIDS, or major burns. In certain embodiments, the immunocompromise may be the result of corticosteroid administration, such as for example corticosteroid administration in conjunction with solid organ transplants or allogeneic hematopoietic cell transplants. The compositions may likewise be administered to a healthy subject. In certain embodiments, the compositions may be administered to a healthy subject in anticipation of an impending immunocompromise. In other embodiments, the compositions may be administered to a healthy subject with no anticipated immunocompromise, such as a solid organ or allogeneic hematopoietic cell donor. In embodiments wherein the compositions are administered in conjunction with solid organ transplants or allogeneic hematopoietic cell transplants, the compositions may be administered to the organ or cell recipient, to the organ or cell donor, or to both the donor and the recipient.

The compositions provided herein may be administered to a subject by any administration route known in the art, including without limitation, oral, enteral, buccal, nasal, intranasal, topical, rectal, vaginal, aerosol, transmucosal, epidermal, transdermal, ophthalmic, pulmonary, and/or parenteral administration. For example, the nasal and/or intranasal administration refers to the delivery of an *Aspergillus fumigatus* Asp f 3 composition across the nasal mucous epithelium and into the peripheral circulation. Conjunctival administration refers to the delivery of an *Aspergillus fumigatus* Asp f 3 composition across the corneal and conjunctival surface into the eye. Buccal administration refers to the delivery across the buccal or lingual epithelia into the peripheral circulation. Oral administration refers to the delivery of an *Aspergillus fumigatus* Asp f 3 composition through the buccal epithelia but predominantly swallowed and absorbed in the stomach and alimentary tract. Rectal administration refers to the delivery of an *Aspergillus fumigatus* Asp f 3 composition via the lower alimentary tract mucosal membranes into the peripheral circulation. Vaginal administration refers to the delivery of an *Aspergillus fumigatus* Asp f 3 composition through vaginal mucous membrane into the peripheral circulation. Parenteral administration refers to an administration route that typically relates to injection which includes but is not limited to intravenous, intramuscular, intraarterial, intrathecal, intracapsular, intraorbital, intra cardiac, intradermal, intraperitoneal, transtracheal, subcutaneous, subcuticular, intraarticular, subcapsular, subarachnoid, intraspinal, and/or intrasternal injection and/or infusion.

In certain embodiments of the invention, an *Aspergillus fumigatus* Asp f 3 composition is administered to a subject intranasally or subcutaneously.

The term "pharmaceutically acceptable carrier" as used herein means a pharmaceutically-acceptable material, composition or vehicle, such as a liquid or solid filler, diluent, excipient, solvent or encapsulating material, involved in carrying or transporting an *Aspergillus fumigatus* Asp f 3 vaccine preparation from one tissue, organ, or portion of the body, to another tissue, organ, or portion of the body. Each carrier must be "pharmaceutically acceptable" in the sense of being compatible with the other ingredients, e.g., an *Aspergillus fumigatus* Asp f 3 vaccine preparation, of the formulation and suitable for use in contact with the tissue or organ of subjects without excessive toxicity, irritation, allergic response, or other problems or complications, commensurate with a reasonable benefit/risk ratio. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Typically, an *Aspergillus fumigatus* Asp f 3 vaccine preparation and/or composition is given to a subject in the form of formulations or preparations suitable for each administration route. The formulations useful in the methods of the present invention include one or more *Aspergillus fumigatus* Asp f 3 vaccine preparation, one or more pharmaceutically acceptable carriers therefore, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of an *Aspergillus fumigatus* Asp f 3 vaccine preparation which can be combined with a carrier material to produce a pharmaceutically effective dose will generally be that amount of an *Aspergillus fumigatus* Asp f 3 vaccine preparation which produces a therapeutic effect, which for example allows a subject vaccinal to *Aspergillus*. Generally, out of one hundred percent, this amount will range from about 1 percent to about ninety-nine percent of the *Aspergillus fumigatus* Asp f 3 vaccine preparation, preferably from about 5 percent to about 70 percent.

Methods of preparing these formulations or compositions include the step of bringing into association an *Aspergillus fumigatus* Asp f 3 vaccine preparation with one or more pharmaceutically acceptable carriers and, optionally, one or more accessory ingredients. In general, the formulations are prepared by uniformly and intimately bringing into association an *Aspergillus fumigatus* Asp f 3 vaccine preparation with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an *Aspergillus fumigatus* Asp f 3 vaccine preparation as an active ingredient. A compound may also be administered as a bolus, electuary, or paste.

In solid dosage forms for oral administration (e.g., capsules, tablets, pills, dragees, powders, granules and the like), an *Aspergillus* vaccine preparation is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate, (5) solution retarding agents, such as paraffin, (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of an *Aspergillus fumigatus* Asp f 3 vaccine preparation therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the *Aspergillus fumigatus* Asp f 3 vaccine preparation(s) only, or preferentially, in a certain portion of the gastrointestinal tract, optionally, in a delayed manner. Examples of embedding compositions which can be used include polymeric substances and waxes. The *Aspergillus fumigatus* Asp f 3 vaccine preparation can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the *Aspergillus fumigatus* Asp f 3 vaccine preparation, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to an *Aspergillus fumigatus* Asp f 3 vaccine preparation, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more *Aspergillus fumigatus* Asp f 3 vaccine preparation with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Formulations which are suitable for vaginal administration also include pessaries, tampons, creams, gels, pastes, foams or spray formulations containing such carriers as are known in the art to be appropriate.

Formulations for the topical or transdermal or epidermal administration of an *Aspergillus fumigatus* Asp f 3 vaccine composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. The ointments, pastes, creams and gels may contain, in addition to an *Aspergillus* vaccine composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the *Aspergillus fumigatus* Asp f 3 vaccine composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

*Aspergillus fumigatus* Asp f 3 vaccine compositions can be alternatively administered by aerosol. For example, this can be accomplished by preparing an aqueous aerosol, liposomal preparation or solid particles containing *Aspergillus* vaccine preparation. A nonaqueous (e.g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Formulations suitable for parenteral administration comprise an *Aspergillus fumigatus* Asp f 3 vaccine preparation in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacterostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e.g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the vaccinal effect of an *Aspergillus fumigatus* Asp f 3 vaccine preparation, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered formulation is accomplished by dissolving or suspending the *Aspergillus fumigatus* Asp f 3 vaccine composition in an oil vehicle.

Injectable depot forms are made by forming microencapsule matrices of an *Aspergillus fumigatus* Asp f 3 vaccine preparation or in biodegradable polymers such as polylactide-polyglycolide. Depending on the ratio of the *Aspergillus fumigatus* Asp f 3 vaccine preparation to polymer, and the nature of the particular polymer employed, the rate of drug release can be controlled. Examples of other biodegradable polymers include poly (orthoesters) and poly (anhydrides). Depot injectable formulations are also prepared by entrapping an *Aspergillus fumigatus* Asp f 3 vaccine preparation or composition in liposomes or microemulsions which are compatible with body tissue.

In a preferred embodiment of the invention, an *Aspergillus fumigatus* Asp f 3 vaccine composition is delivered to a subject in a therapeutically effective dose. The term "pharmaceutically effective dose" as used herein refers to the amount of the *Aspergillus* vaccine preparation and/or an *Aspergillus fumigatus* Asp f 3 vaccine composition, which is effective for producing a desired vaccinal effect. As is known in the art of pharmacology, the precise amount of the pharmaceutically effective dose of an *Aspergillus* vaccine preparation that will yield the most effective results in terms of efficacy of treatment in a given subject will depend upon, for example, the activity, the particular nature, pharmacokinetics, pharmacodynamics, and bioavailability of a particular *Aspergillus fumigatus* Asp f 3 vaccine preparation, physiological condition of the subject (including race, age, sex, weight, diet, disease type and stage, general physical condition, responsiveness to a given dosage and type of medication), the nature of pharmaceutically acceptable carriers in a formulation, the route and frequency of administration being used, to name a few. However, the above guidelines can be used as the basis for fine-tuning the treatment, e.g., determining the optimum dose of administration, which will require no more than routine experimentation consisting of monitoring the subject and adjusting the dosage. Remington: *The Science and Practice of Pharmacy* (Gennaro ed. 20$^{th}$ edition, Williams & Wilkins PA, USA) (2000).

Having generally described the present invention, the same will be better understood by reference to certain specific examples, which are set forth herein for the purpose of illustration.

EXAMPLES

Example 1

Preparation of *A. fumigatus* Viable Conidia and Hyphal Sonicate

The *A. fumigatus* strain AFCOH1, isolated from an IPA patient at the City of Hope National Medical Center (Duarte, Calif.) was used for vaccine preparations and infection as described previously (Ito 2002). Conidia stock suspensions were prepared by collecting spores from 5-7-day cultures on potato dextrose agar (BD/Difco) grown at 37° C. into sterile 0.9% saline containing 0.1% Tween 80. Clumps of conidia were dispersed with 3-mm glass beads, and the suspension was washed twice and suspended to the desired concentration with 0.9% saline containing 0.01% Tween 80 (or alternatively 1% n-octyl-β-D-gluco-pyranoside) and 30% glycerol. Aliquots were frozen at −80° C. and quick thawed to 37° C. prior to use. This procedure gave mycelia-free suspensions of conidia with >95% single conidia. Conidia were enumerated with a hemocytometer, and viability was assessed by agar plating.

Crude hyphal extract was prepared by sonication of hyphal mass from 72 hour cultures grown in Czapek Dox medium supplemented with 1% Tryptone (BD/Difco). This hyphal sonicate (HS) is not sterile and contains some viable hyphal fragments in a complex mixture of released hyphal proteins and other cellular components.

Example 2

Identification of Vaccine Candidates

CF-1 female mice (Charles River Labs, H2-k MHC Class 1 haplotype) were purchased at 7 weeks of age and were allowed to acclimate for at least one week prior to use. All experiments were conducted in a BL-2 containment facility in compliance with animal care regulations and under care and use protocols approved by the institutional research animal care committee.

Figure 3:
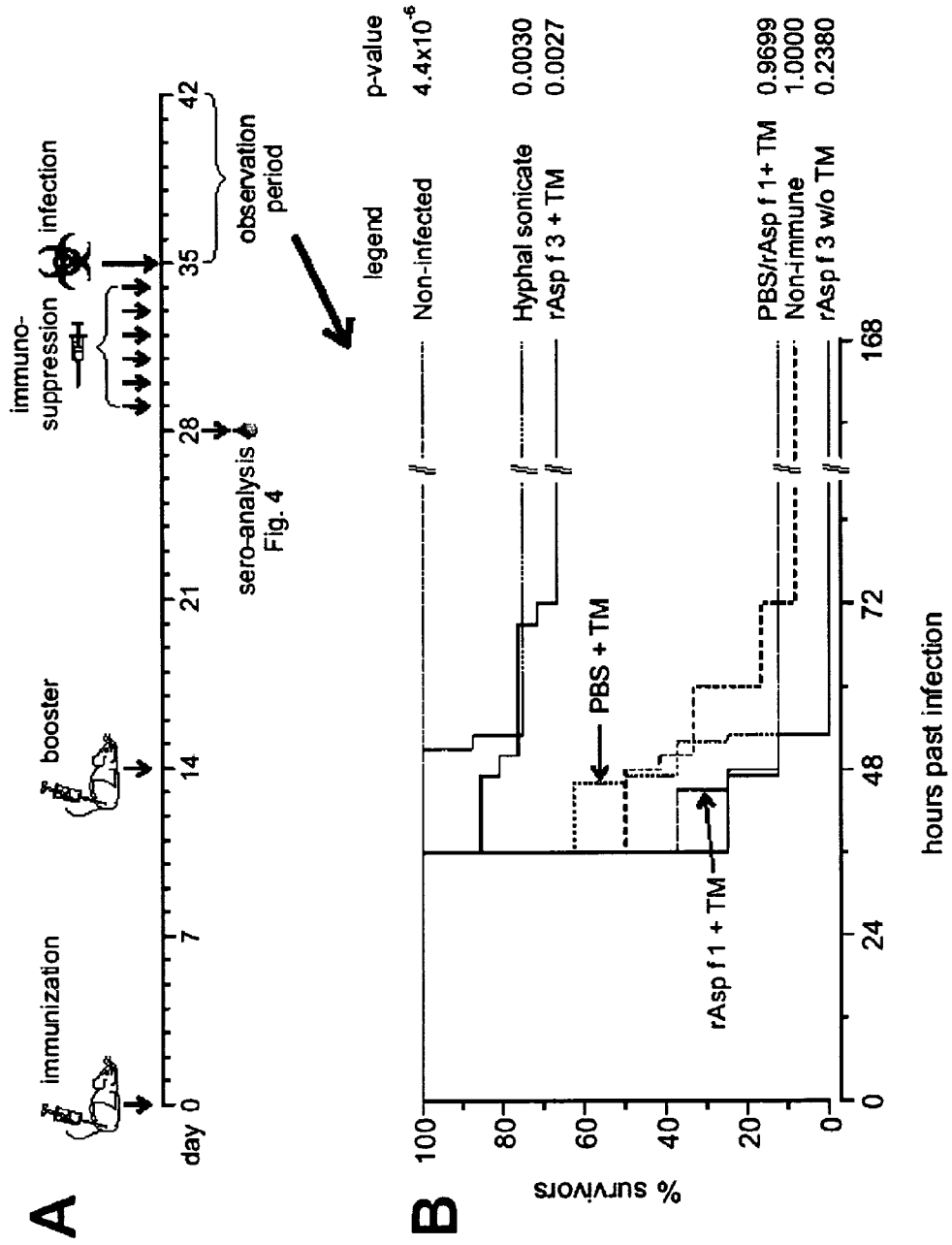
FIG. 3: (A) Experimental scheme of immunization, immunosuppression and challenge. (B) survival curves recorded during the observation period. Number of animals per group were: 16 non-infected controls, 8 hyphal sonicate, 21 rAsp f 3+TITERMAX® adjuvant (TM), 8 PBS+TM, 8 rAsp f 1+TM, and 12 non-immune controls that received PBS injections instead of antigens or adjuvant.

Mice were immunized with HS or viable conidia (VC), immunosuppressed, and challenged with *A. fumigatus* conidia using the protocol set forth in FIG. 3A. Mice were vaccinated twice, two weeks apart. Vaccination with HO was carried out subcutaneously at the base of the tail using 40 μL of HS. HS was administered neat as a 1:1 (vol/vol) emulsion in TITERMAX® (TM, from TiterMax, Inc., Norcross, Ga.) prepared according to the manufacturers instructions. Vaccination with VC was carried out via naso-pulmonary exposure.

Immunosuppression was generated by subcutaneous cortisone acetate administration in 2.5-mg doses for six consecutive days prior to challenge, commencing two weeks after the second immunization (FIG. 3A). To reduce the risk of bacterial infection associated with immunosuppression, mice were prophylactically provided acidified water containing Sulfatrim® (Alpharma), and were administered 200 μg of levofloxacin (Levaquin®, Ortho-McNeil) subcutaneously 1 hour prior to infection. Under light ketamine/xylazine anesthesia, mice were intranasally inoculated with 30 μL of conidial suspension containing 3×10$^6$ viable conidia while being held in the vertical position, and were placed on their backs during recovery from anesthesia.

After inoculation, all animals fully recovered within 1-2 hours, and were normal in appearance until signs of disease became apparent 24-30 hours after infection. Mice were observed on a regular basis during the day, and were weighed each morning. Body temperature was taken in the morning and evening with a digital thermometer inserted into the vagina. Time of death or euthanasia was recorded and deaths that occurred at night were assigned a time of death midway between the last evening observation and first morning observation. Criteria for euthanasia were labored breathing, a 20% weight loss, and severe hypothermia (<32° C.). Time of death data were analyzed by the Mann-Whitney U-Test (equivalent to Wilcoxon Rank Sum Test). Disease pathology and the fungal distribution within the lung parenchyma were performed on formalin-fixed, paraffin-embedded, sections of lung tissue using standard hematoxylin and eosin (HE) and Gomori methenamine silver (GMS) stains. Microscopy was performed on an Olympus AX70 Model U-MPH Microscope (Tokyo, Japan) with QImaging RETIGA EXi camera and the ImageProPlus 5.1 software.

As shown previously, subcutaneous injection of HS and naso-pulmonary exposure to VC was protective to CF-1 mice under cortisone acetate-induced immunosuppressive conditions (Ito 2002).

Figure 6:
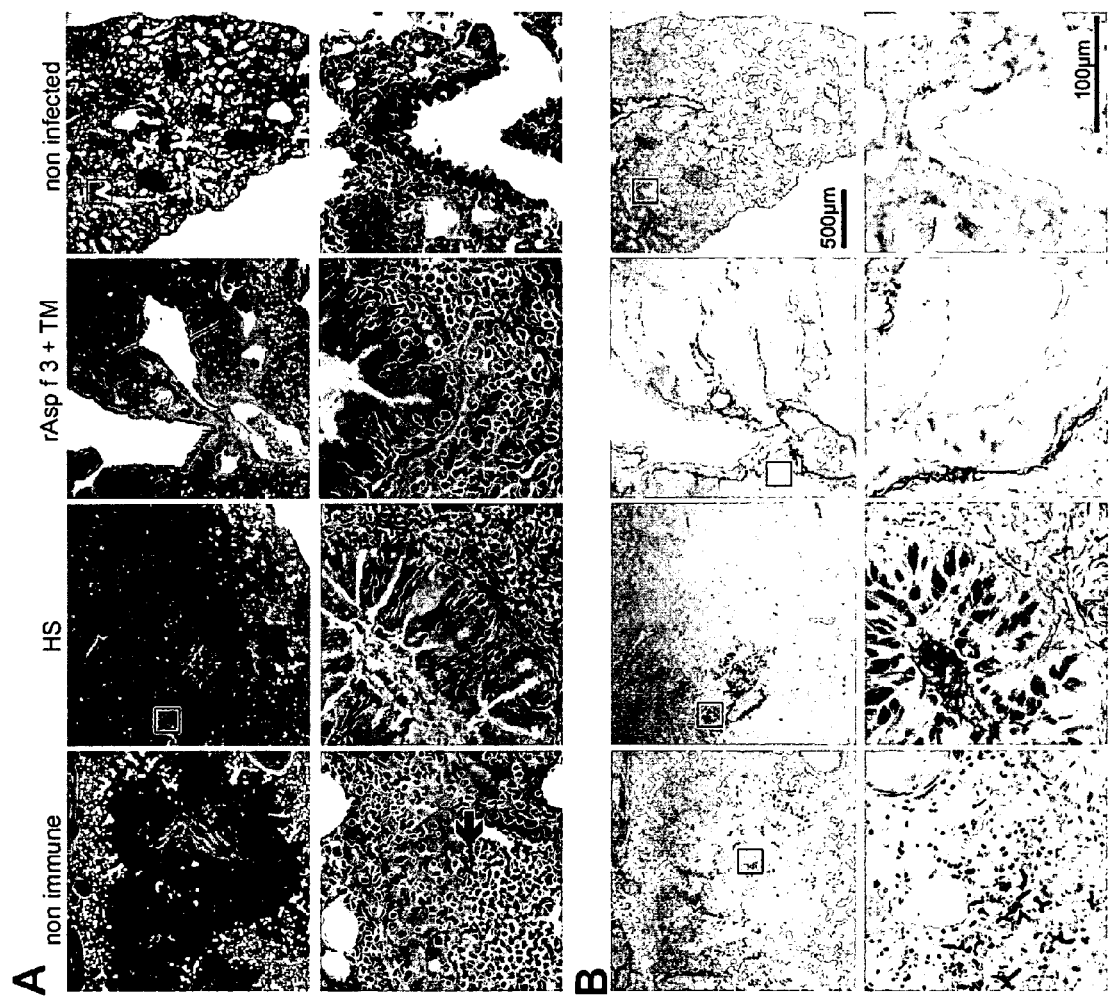
FIG. 6: Histology. (A) Hematoxylin-and-Eosin (HE) and (B) Gomori-silver staining of consecutive slices of formalin-fixed lungs of: a succumbed non-immune animal (far left column), an HS-vaccinated survivor (second column), an rAsp f 3+TM-vaccinated survivor (third column), and a non-infected mouse (far right column). Magnifications for the first row in A and B are 20-fold and 200-fold for each second row. When displayed, squares denote regions chosen for the higher magnification. The black arrow points to a hyphal structure.

Infected non-immune individuals that died as a result of IPA demonstrate a fairly compact peribronchial infiltrate, consisting predominantly of polymorphonuclear leukocytes (PMN), with few histiocytes and lymphoid cells. Numerous PMN are found in the bronchial lumens. The adjacent parenchyma has edema and some hemorrhage (FIG. 6A, far left). Gomory-silver stain reveals numerous hyphal elements in the bronchial lumen and in the infiltrate around the bronchials (FIG. 6B, far left). HS-immunized survivors have a very dense peribronchial mononuclear cell infiltrate that is composed of lymphoid cells, plasma cells and histiocytes. The bronchial epithelium is hypersecretory, but the lungs are free of hyphae (FIG. 6, second column).

Individual sera from immunized mice that exhibited notable protection against IPA were analyzed by Western blot for their content of antigen-specific immunoglobulin. HS was subjected to electrophoresis on reducing BisTris SDS Nu-PAGE gels (4-10%, Invitrogen). Proteins were transferred to PVDF membrane (0.22 μm, BioRad), using the Xcell II (Invitrogen). Membranes were blocked at 4° C. overnight in 5% milk, 0.24% Tris base, 0.8% NaCl, 0.01% tween-20, adjusted to pH 7.6 with ~1.2 mM HCl (final concentration). To analyze sera from multiple individuals, membranes blotted with HS from a single-slot SDS-PAGE gel were cut into strips of 5 mm width (cut alongside the direction of separation) and probed in 1.2 mL volumes of serum in milk, 1:2500, in Accutran disposable incubation trays with multiple channels (Schleicher & Schuell, Inc., Keene, N.H.). Goat anti-mouse IgG-HRP-conjugated secondary antibodies were used in dilutions of 1:3000 to 1:20,000 in accordance with manufacturer's instructions for chemiluminescent detection on X-ray films.

Sera from HS-vaccinated mice contained IgG antibodies with varying specificities to *A. fumigatus* antigens (FIG. 1A). In contrast, IgG from the VC-vaccinated animals reacted predominantly with antigen molecules at approximately 19 kDa (FIG. 1B).

The presence of antibodies against Asp f 3, dipeptidyl peptidase and catalase in serum pooled from mice surviving *A. fumigatus* infection had been observed in earlier immunoprecipitation experiments that utilized immobilized protein-A as the antibody capturing matrix. Attempts to immunoprecipitate fungal protein with much lower antibody amounts from single mice produced inconsistent results, but such antibodies proved useful for the tracing of antigens during fractionation and chromatography.

HS was prefractionated by ultrafiltration through Centricons (Millipore) with 30 kDa MWCO and then with 10 kDa MWCO. Crude CF as well as prefractionated HS retentate and filtrate of the 10 kDa MWCO fraction were analyzed by Western Blot analysis.

The serum from VC-exposed mice clearly reacts with a 19-kDa antigen found in the 10-to-30 kDa fraction of CF and HS (FIG. 1C). The antigen from HS is not identical to Asp f 1, a known 19-kDa antigen and major allergen detected only extracellularly in CF using a monoclonal anti-Asp f 1 antibody (FIG. 1C).

The HS-retentate of the 10-kDa membrane was further fractionated by reversed phase HPLC (column: Jupiter 5μ C18 300A, 250×4.6 mm, Phenomex, Calif.) with a gradient of acetonitrile/water in 0.1% trifluoroacetic acid (Instrument: ÄKTA purifier, GE Healthcare). Fractions were spotted on nitrocellulose membrane (Biorad) and dot blots were developed with sera from VC and HS-immunized mice or monoclonal anti-Asp f 1 antibodies and anti-mouse IgG:HRP, diluted 1:3000, for chemiluminescent detection. Positive fractions were separated by SDS gel electrophoresis and stained with GelCode blue (PIERCE).

Figure 2:
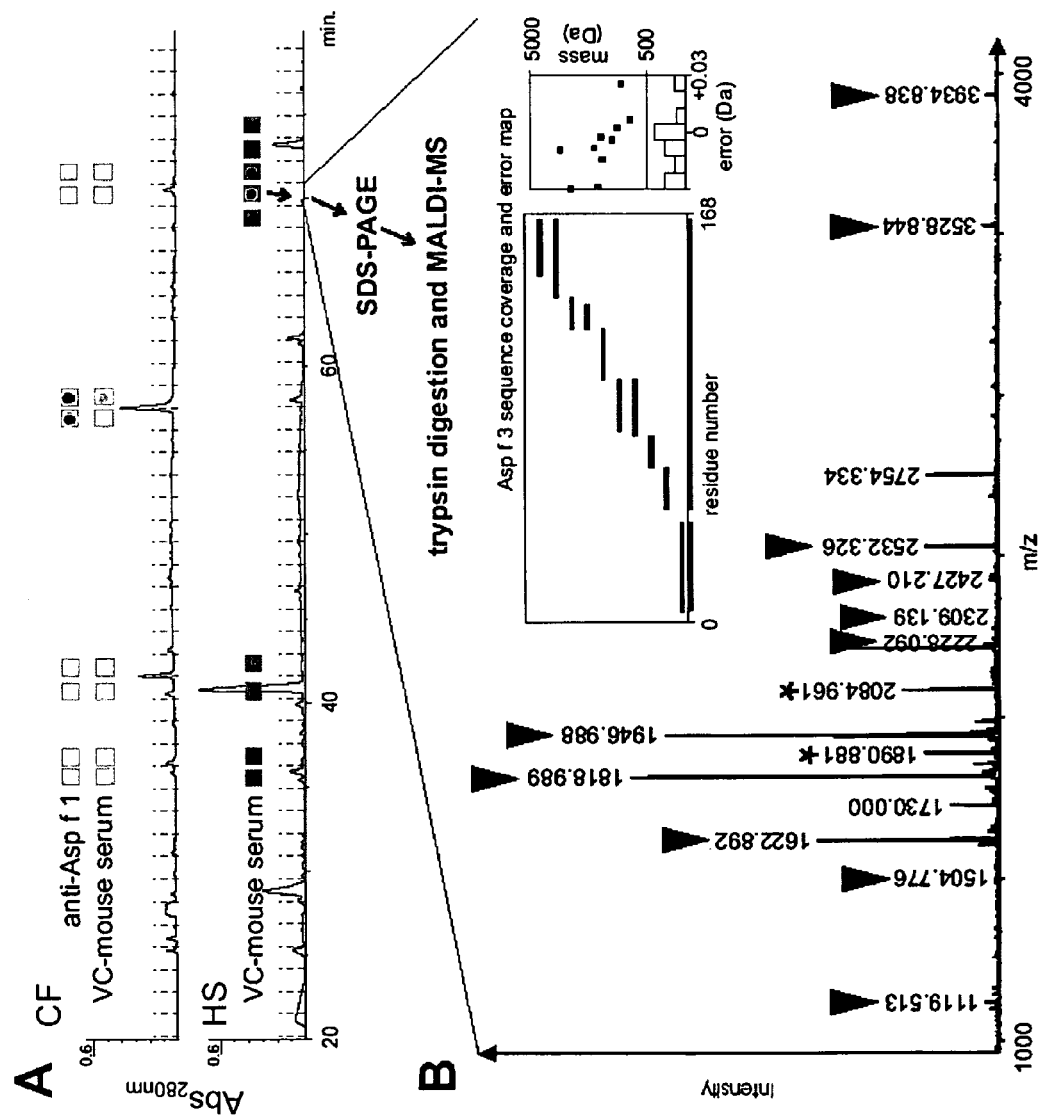
FIG. 2: (A) Reversed phase HPLC separation and dot-blot analysis of culture filtrate (CF) and pre-fractionated hyphal sonicate (HS). The input was the 10-to-30-kDa HS fraction from ultrafiltration. The 70-minute HPLC faction of HS reacts positively with serum from VC immunized mice. (B) MALDI-MS analysis of a 19-kDa band of this fraction identifies *A. fumigatus* Asp f 3 as the major protein component. Black triangles denote assigned peptide ions that match the Asp f 3 sequence. Stars denote two peptide ions from cofilin that were assigned based on MS/MS data of these ions.

Asp f 1 was detected by dot blot in 10-kDa retentate fractions of CF eluting at ~57 minutes using the monoclonal anti-Asp f 1 antibody (FIG. 2A). The same fraction also showed weak reaction with serum from VC-exposed mice.

A 70 minute fraction of the HS retentate reacted strongly with IgG from VC-immune mice. This fraction was further separated by SDS-PAGE (not shown) and the protein content of an 18-20-kDa band was reduced, alkylated, trypsin-digested and analyzed by MALDI-Q-TOF and MALDI-Q-ion trap mass spectrometry (FIG. 2B). Excised gel bands were placed on needle-punctured V-shaped microtiter plates (Greiner) and robotically processed using a Genesis Proteam 100 liquid handling system (Tecan) with a customized procedure encompassing gel destaining in 50% acetonitrile, 100 mM ammonium bicarbonate (ABC), protein reduction in 10 mM tris(carboxyethyl phosphine) (PIERCE), 50 mM ABC, alkylation with iodoacetamide followed by 8 hr digestion with trypsin at 37° C. Digest peptides were captured on reversed phase Poros 20 R 2 beads (Applied Biosystems Inc.), collected on ZipTips (Millipore) and eluted onto stainless steel sample plates and co-crystallized with α-cyano-4-hydroxy cinnamic acid as MALDI-MS matrix. Single-stage mass spectrometric analyses were performed on a Protof2000 MALDI-quadrupole time-of-flight instrument (PerkinElmer/Sciex) an multistage mass spectrometric fragmentation spectra were obtained on a self-built MALDI-quadrupole ion trap essentially as previously described (Krutchinsky 2001; Kalkum 2003). Spectra were analyzed by database searching using Profound, Xproteo and The GPM X! Tandem.

Peptide-mass fingerprinting as well as MS/MS data identified the known allergen Asp f 3 (accession # XP_747849, SEQ ID NO:6) as the major component of the IgG-binding HPLC fraction with an unusually high sequence coverage of about 93%. A few digest peptides of peptidylprolyl cis-trans isomerase (cyclophilin, PPlase, Asp f 11, accession # XP_749504) and cofilin (accession # XP_753587) were also detected in the same band, indicating the presence of these proteins as minor impurities. Taken together, this data indicates that mice infected with viable conidia produce specific antibodies predominantly against Asp f 3 and at lower levels against Asp f 1.

Example 3

Construction and Expression of Recombinant Asp f 1 and 3

Purified recombinant His-tagged Asp f 3 (rAsp f 3, SEQ ID NO:7) and Asp f 1 (rAsp f 1) were produced. Asp f 1 was expressed from the pQEMW1 plasmid (Drs. Frank Ebel and Jürgen Heesemann, LMU Munich, Germany), using an M15 *E. coli* host strain containing the repressor plasmid pREP4 (Qiagen) as described (Weig 2001). Asp f 3 and its truncated forms were cloned and expressed using a pQE30Xa vector (Qiagen). In brief, total mRNA was obtained from ground hyphae using the RNeasy mini kit (Qiagen), reverse transcribed with the Superscript II kit (Invitrogen), and PCR amplified with PCR primers 1 (SEQ ID NO:1) and 2 (SEQ ID NO:2), which contain a SacI and KpnI site, respectively. pQE30Xa and the primers were restricted with SacI/KpnI and ligated using T4 ligase (all from New England Biolabs) (Sambrook 2001). The resulting plasmid, designated pMK2Aspf3, was transformed into *E. Coli* M15[pREP4] and selected on Luria-Bertani agar plates with 100 μg/mL ampicillin and 25 μg/mL kanamycin. An N-terminal deletion of Asp f 3 containing residues 15-168 (SEQ ID NO:8), was produced by partial amplification of the insert sequence from pMK2Aspf3 with PCR primers 2 and 3 (SEQ ID NO:3). PCR primer 3 contains a StuI site. pQE30Xa and the PCR product were digested with StuI/KpnI, ligated, and selected as described above, yielding pMK2Aspf3(15-168). C-terminally truncated rAsp f 3 (1-142) (SEQ ID NO:9) and the bipartite N/C-terminal truncation rAsp f 3 (15-142) (SEQ ID NO:10) were obtained by introduction of a stop codon at K143 into the sequences of pMK2Aspf3 and pMK2Aspf3(15-168), respectively, using the QuikChange kit (Stratagene) with PCR primers 4 and 5 (SEQ ID NOs: 4 and 5, respectively), which mismatch the Asp f 3 sequence at the base pair corresponding to residue 13 in each primer. DNA sequencing, performed at the DNA Sequencing Core Lab of the City of Hope, verified the construct sequences.

Proteins were expressed at 37° C. in 1-L *E. coli* cultures with LB medium after IPTG induction (Sambrook 2001) and purified from lysed cells using self-packed Ni-NTA agarose columns and urea-containing lysis, wash and elution buffers (Qiagen). Identities of the purified recombinant proteins were confirmed by peptide mass fingerprinting of gel-separated products. Protein concentrations were determined by Bradford (Bradford 1976) protein assay (B10-Rad).

Example 4

Vaccination with Asp f 3 and 1

Purified rAsp f 3 and rAsp f 1 were tested as vaccines in a CF-1 murine model of IPA using the vaccination schedule set forth in FIG. 3A. Vaccinations with HS as set forth in Example 2, above, served as a positive control (protection expected), while mock immunizations with either phosphate buffered saline (PBS) or the TITERMAX® (TM)-adjuvant alone were used as negative controls (no protection expected). Mice were vaccinated twice, two weeks apart, subcutaneously at the base of the tail. rAsp f 1 was administered neat, as a 1:1 (vol/vol) emulsion in TITERMAX® (TM, from TiterMax, Inc., Norcross, Ga.) prepared according to the manufacturers instructions. Mice were immunosuppressed and infected with viable conidia as set forth in Example 2, above. Prior to immunosuppression, blood was taken from a small tail vein incision, diluted 1:20 in PBS, and the diluted plasma was separated by centrifugation, pooled, and frozen at −80° C. for later testing by Western or dot blot.

Mice immunized with the major allergen rAsp f 1 produced antibodies only against rAsp f 1, and the associated immune response was not protective.

Approximately 65% of the rAsp f 3-vaccinated mice survived (p<0.003, FIG. 3B), a degree of protection comparable to that achieved with crude HS-vaccinations (p=0.003). None of the immunizations was fatal (see non-infected controls, p=4.4×10$^{-6}$, FIG. 3B). The rAsp f 3 vaccine induced a protective immune response only in presence of the TM-adjuvant. Subcutaneous injections of Asp f 3 without TM, as well as Asp f 1 with TM, and mock immunizations with either PBS or TM alone were not protective. Differences in survival times between these latter four groups were not statistically relevant.

Histopathological analysis revealed that lungs of Asp f 3/TM-vaccinated mice were free of hyphae. They showed a patchy, bronchiocentric mononuclear cell infiltrate (FIG. 6, third column), which is less dense than in the HS-vaccinated animals. The infiltrate in Asp f 3/TM-vaccinated mice has fewer large lymphoid cells and the lungs are less consolidated than the HS-vaccinated case. In contrast to non-immune animals, no significant intrabronchial inflammatory component could be found.

Figure 4:
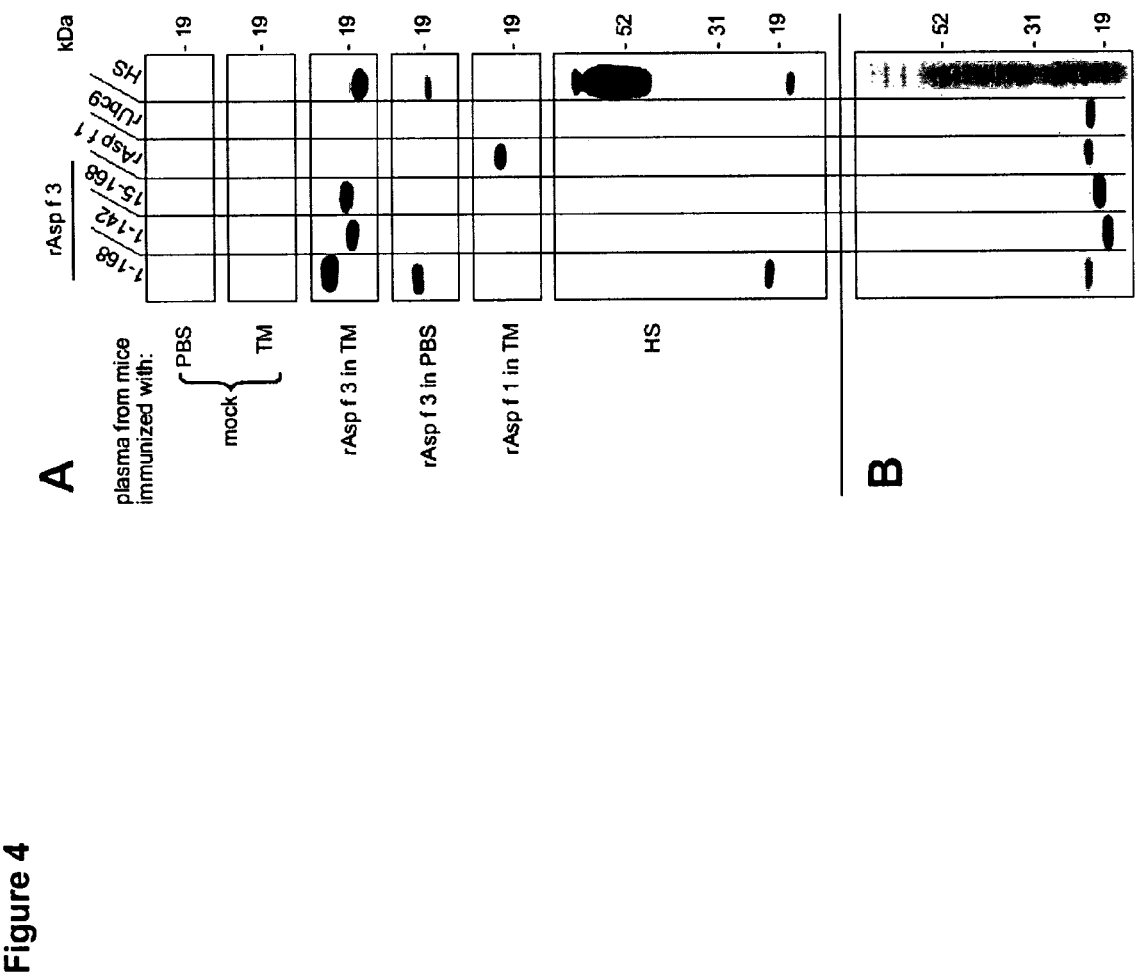
FIG. 4: Serological analysis of immunized mice. (A) Western blots with recombinant proteins, full-length and truncated rAsp f 3s, rAsp f 1, rUbc9 and hyphal sonicate (HS) were developed with pooled plasma from mice obtained on the day before immunosuppression. Rat-anti-mouse IgG2a:HRP served as secondary antibody. (B) Coomassie-stained SDS gel indicates comparable amounts of recombinant proteins that served as the input for the Western blots in (A).

Plasma samples taken prior to immunosuppression were used to probe Western blots with different versions of rAsp f 3, rAsp f 1, rUbc9 (Liu 1999), and HS (FIG. 4A). The recombinant proteins were loaded at comparable levels (0.4 μg/lane) as determined by Bradford and as indicated by the GelCode blue-stained gel in FIG. 4B. Antigen-specific IgG2a was detected in initial experiments to be the dominant immunoglobulin subclass in the sera of immunized animals, which is consistent with a $T_H1$-type immune response expected when using the TM adjuvant. Western blots were therefore developed with a monoclonal HRP-conjugated anti-mouse IgG2a antibody (FIG. 4A). IgG2a against full-length rAsp f 3 (168 amino acids plus His tag) was detected in the sera of animals vaccinated with rAsp f 3 or HS. Natural non-His-tagged Asp f 3 is responsible for the signal below 19 kDa on the lanes of blotted HE. The C- and N-terminally truncated versions of rAsp f 3, spanning residues 1-142 and 15-168, respectively, reacted only with sera from mice vaccinated with rAsp f 3 plus adjuvant. Similar truncated versions have been reported to lack the ability to bind human IgE from ABPA patients (Ramachandran 2002). Accordingly, such engineered proteins no longer possess the IgE-binding property by which most *A. fumigatus* allergens have been defined (Kodzius 2003). IgG2a from sera of HS-immunized animals reacts with full length rAsp f 3 but not with the truncated versions, suggesting that the IgG2a epitope responded to in these mice might be similar (if not identical) to the IgE-binding conformational epitope in serum from ABPA patients (Ramachandran 2002). A His-tagged recombinant mouse protein, Ubc9, was included in the blots to determine if any of the recombinant His-tagged vaccines would induce anti-His-tag antibody production. No such antibodies were observed.

Figure 13:
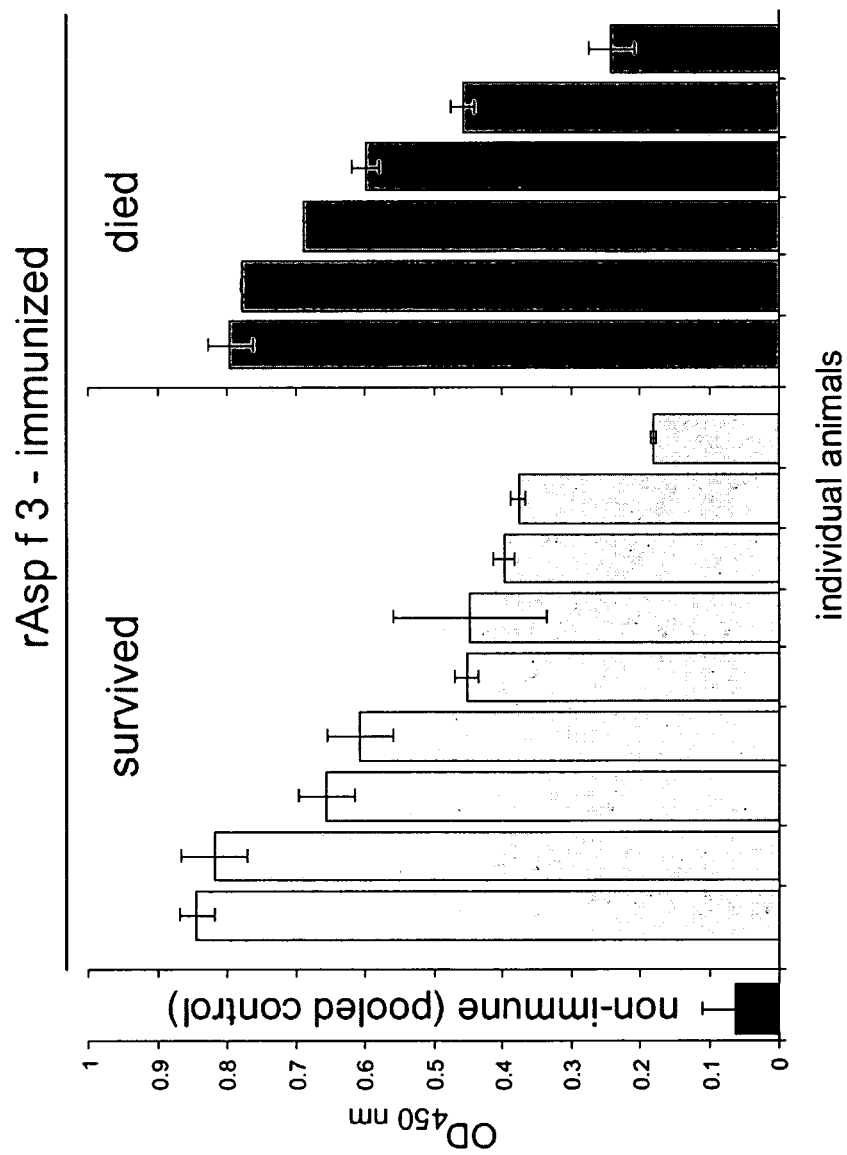
FIG. 13: Asp f 3-specific IgG titers in Asp f 3-vaccinated survivor mice ("survived") versus Asp f 3-vaccinated mice that died of aspergillosis ("died").
Figure 14:
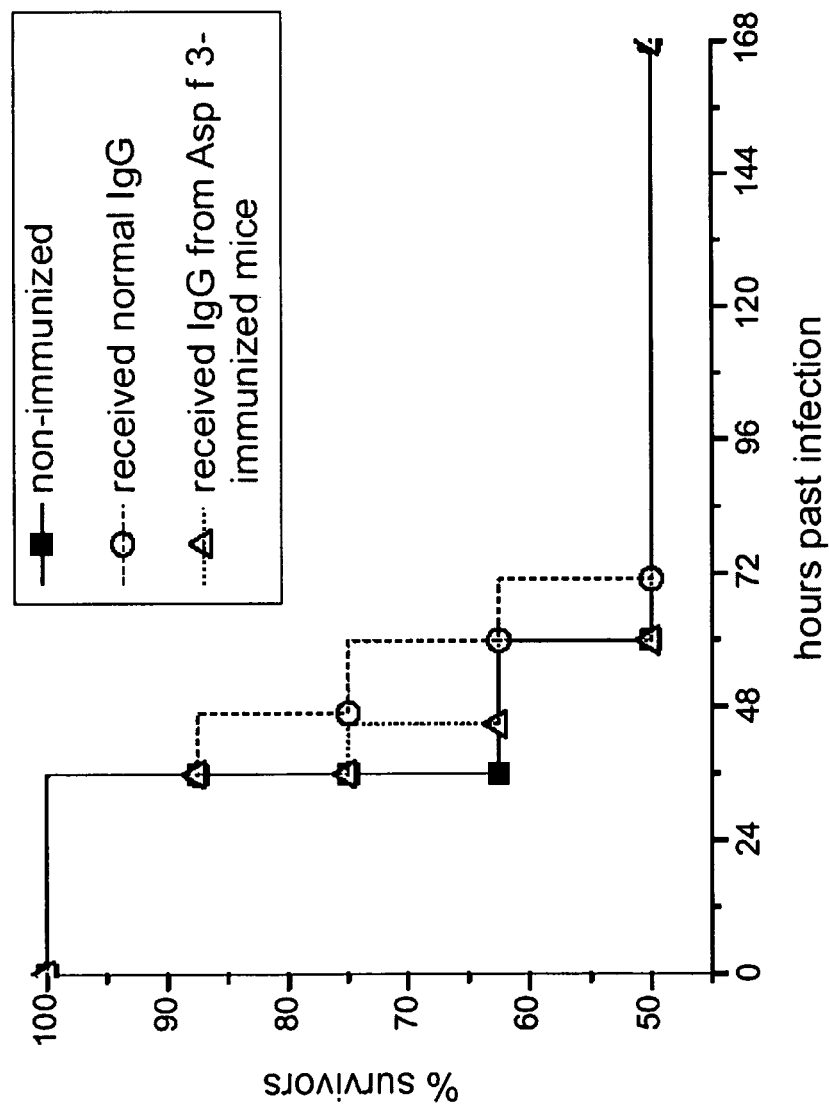
FIG. 14: Anti-Asp f 3 antibodies from rAsp f 3-vaccinated mice do not confer protection to non-immunized mice.

The Asp f 3-specific IgG titers of vaccinated survivors and immunized animals that died from aspergillosis were found to lie in comparable ranges (FIG. 13), suggesting that immunization with Asp f 3 protects through a cell-based mechanism rather than an antibody-based mechanism. To test this hypothesis, IgG antibodies from rAsp f 3-vaccinated animals were transferred intravenously into non-immunized mice. Each recipient mouse received the IgG equivalent of two Asp f 3-vaccinated mice. This transfer did not provide significant protection to the recipient mice (FIG. 14), suggesting that protection is conferred via cell-based mechanism.

Figure 15:
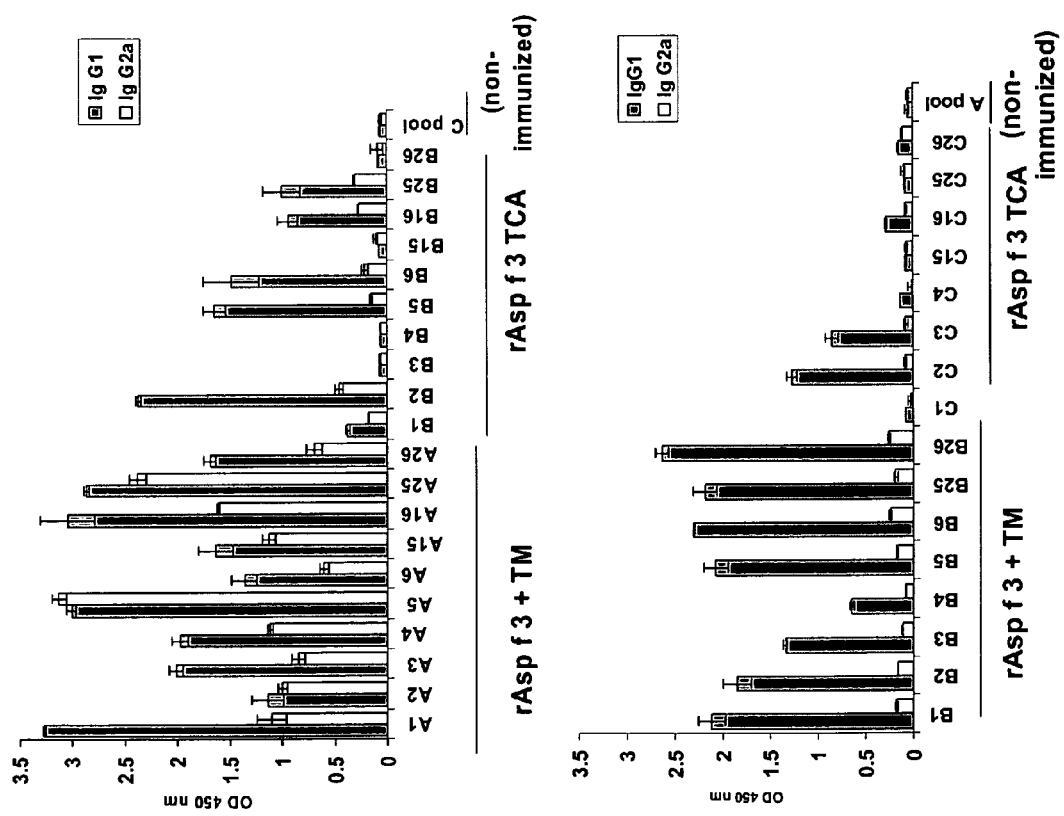
FIG. 15: Anti-Asp f 3 IgG isotypes in vaccinated CF1 mice versus vaccinated DBA/2 mice.

DBA/2 mice were immunized with rAsp f 3 using the same protocol employed for CF-1 mice above. Unlike the CF-1 mice, which displayed a $T_H1$ response, the DBA/2 mice displayed a $T_H2$ response as determined by IgG subtyping (FIG. 15). The CF-1 mice displayed IgG1:IgG2a ratios of 1.62 and 4.23 after vaccination with rAsp f 3 plus TM and rAsp f 3 plus TCA, respectively. The DBA/2 mice, on the other hand, displayed IgG1:IgG2a ratios of 10.96 and 5.23 after vaccination with rAsp f 3 plus Tm and rAsp f 3 plus TCA, respectively. Only the $T_H1$ response correlated with protection. These results suggest that Asp f 3 does indeed protect via a cell-based mechanism.

Example 5

Vaccination with Truncated Asp f 3 and 1

Figure 5:
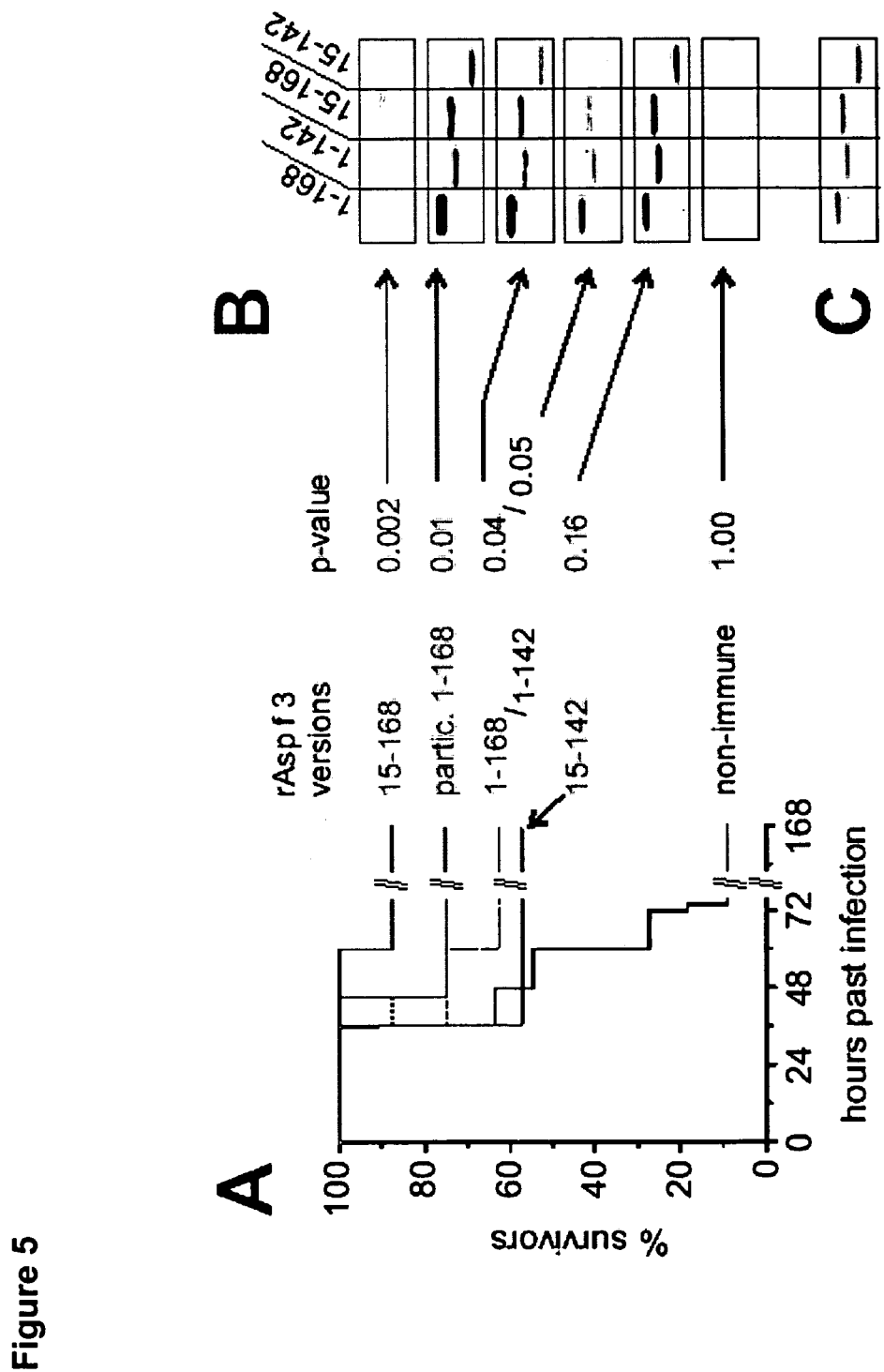
FIG. 5: (A) Survival curves for mice vaccinated with truncated versions of Asp f 3 with TM adjuvant (as indicated by each first and last amino acid residue number) and particulate, adjuvant-free full-length rAsp f 3 (partic. 1-168). (B) Serological analysis of pooled plasma from these mice by Western blot analysis (around 19 kDa). (C) The Coomassie-stained gel indicates comparable loading amounts of the of the rAsp f 3 versions (250 ng/band).

Truncated versions of rAsp f 3, namely residues 15-168, 1-142 and 15-142 of SEQ ID NO:6, were tested to determine whether they could still function as vaccines. Using the same murine model for IPA and TM as adjuvant, it was found that the N-terminal (15-168) and C-terminal (1-142) truncations were similarly protective, with 87% (p<0.002) and 62% (p<0.05) survival, respectively (FIG. 5A). Double truncated rAsp f 3 (15-142) was somewhat protective (57% survivors, p<0.16), suggesting a trend. When compared to full-length rAsp f 3 (1-168), the truncated versions of rAsp f 3 elicit comparable and in some cases even better protection, as demonstrated for the N-terminal truncation.

Western blots with plasma samples from the immunized animals indicate that vaccinations with full-length and double truncated rAsp f 3 (15-142) induce strong specific IgG-responses against all four tested versions of rAsp f 3 (FIG. 5B). Remarkably, these antibody responses are significantly diminished in animals vaccinated with either the N-terminal (15-168) or C-terminal deletion (1-142) protein. IgG from animals vaccinated with the C-terminal truncation reacted stronger with full-length Asp f 3 than with the truncated versions, but IgG from those vaccinated with the N-terminal truncation only yielded weak signals on Western blots with rAsp f 3 (1-142) and rAsp f 3 (15-168) (FIG. 5B).

Example 6

Vaccination with Particulate Asp f 3

Since TM is not suitable for human use and the soluble form of rAsp f 3 was not protective, an adjuvant-free, particulate form of full-length rAsp f 3 was tested. This vaccine was prepared by precipitation with trichloroacetic acid (TCA) and resuspension of the protein pellet in the original volume of PBS with 0.5% methylcellulose. Vortexing in the presence of glass beads produced protein particles that were sufficiently small to pass through a 25-gauge injection needle. The particulate rAsp f 3 was found to be as immunoprotective as the rAsp f 3/TM preparation (FIG. 5A), and induction of specific anti-Asp f 3 antibodies was comparable (FIG. 5B).

Example 7

Identification of T and B Cell Epitopes in rAsp f 3 and *A. fumigatus* Hyphal Protein Extracts CF-1, DBA/2, and BALB/c mice were immunized and boosted with either crude *A. fumigatus* extracts or with rAsp f 3. Mice were then immunosuppressed with cortisone and challenged with viable *A. fumigatus* spores. T cells from lymph nodes and spleens of survivor mice were isolated using magnetic beads, and the T cell were co-cultured with autologous irradiated antigen-presenting cells and rAsp f3 antigens.

Figure 7:
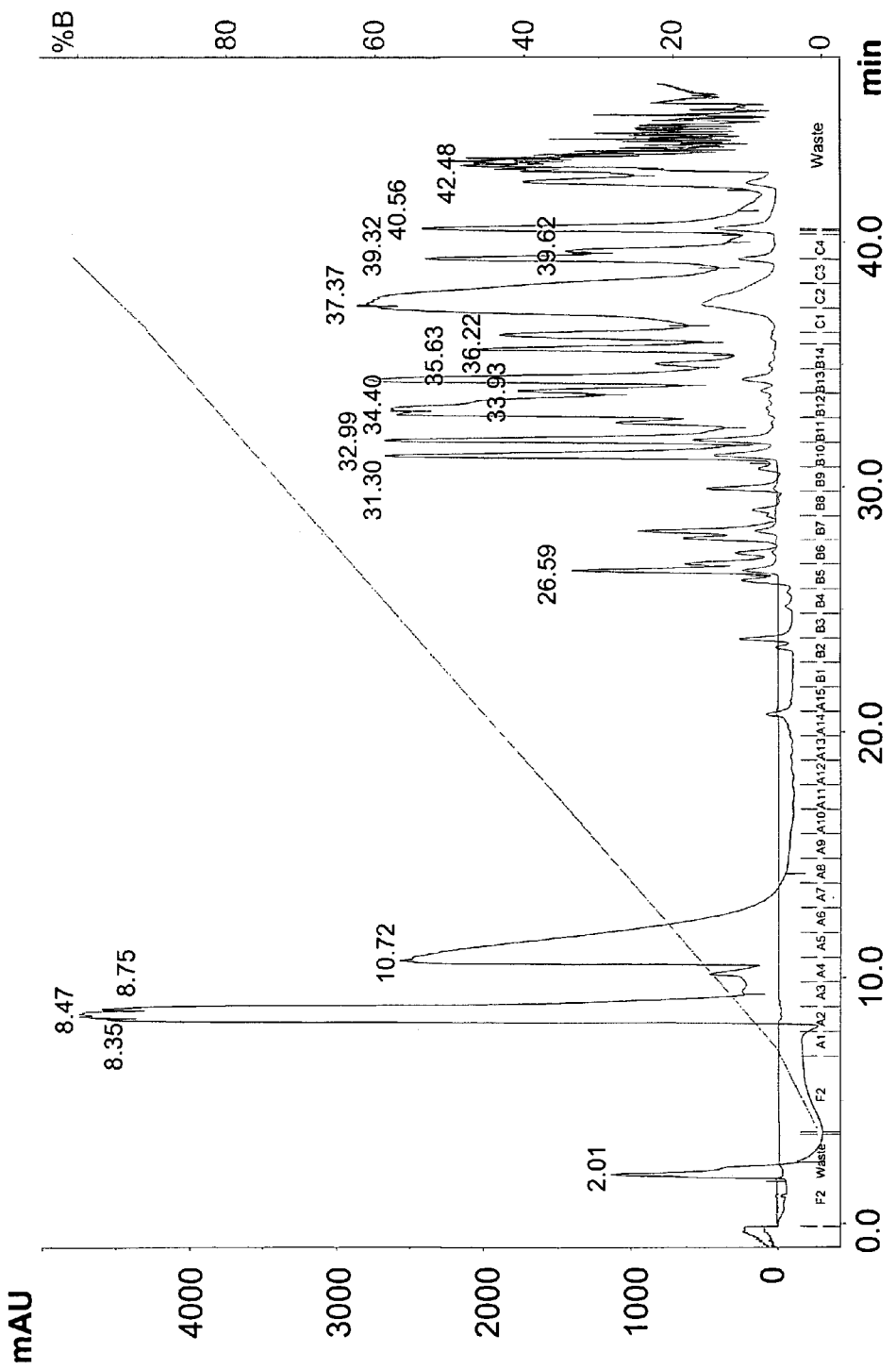
FIG. 7: HPLC chromatogram of tryptic rAsp f 3 digest peptides separated on a reversed phase C18 column.
Figure 8:
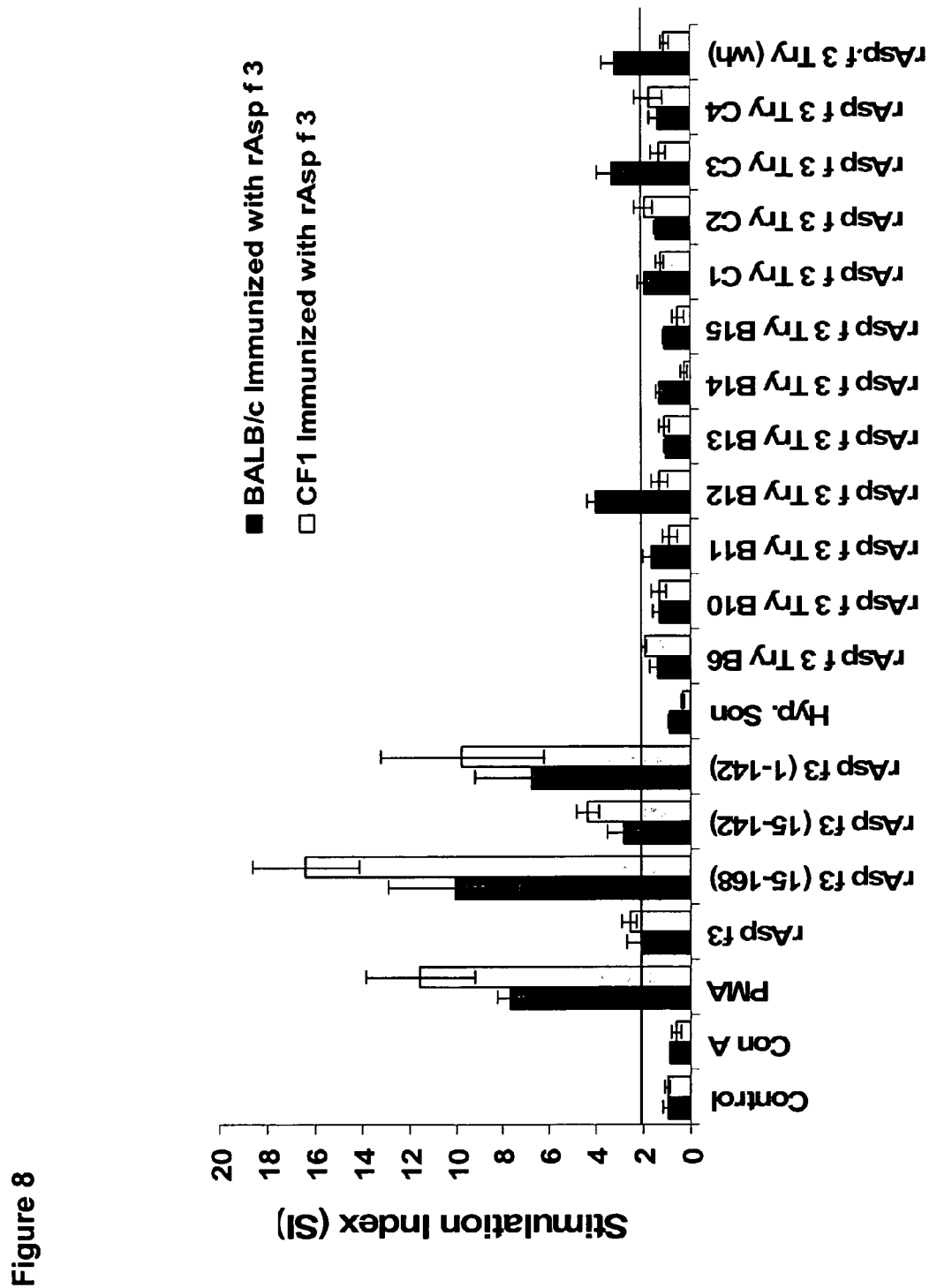
FIG. 8: Lymphoproliferation responses of rAsp f 3-immunized mice to HPLC-separated fractions of tryptic digest rAsp f 3 peptides. Fractions B12 and C3 contain T cell epitopes.
Figure 9:
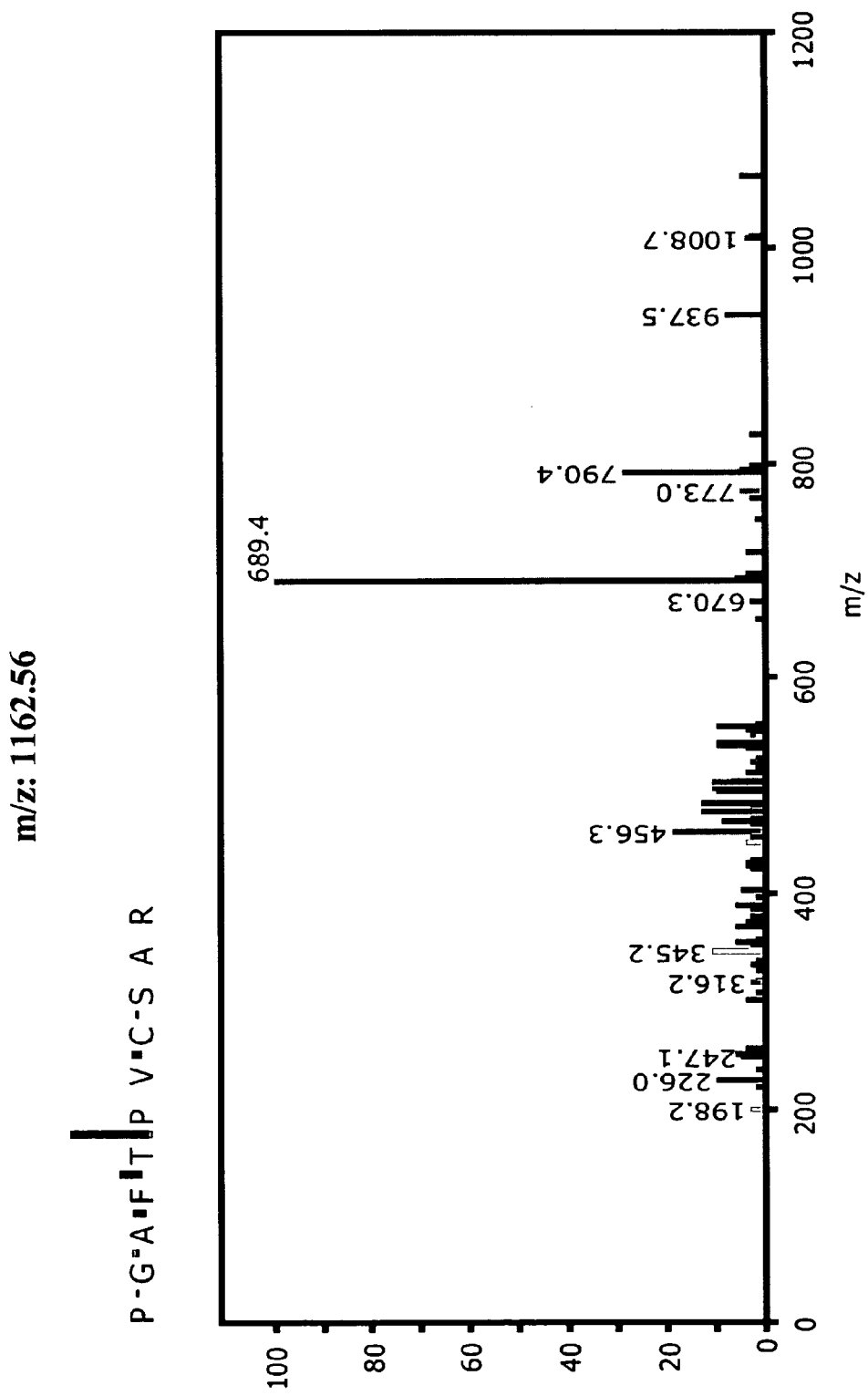
FIG. 9: LC/FTICR-MS/MS spectra of trypsin-digested rAsp f 3 peptides.

To identify T cell epitopes, HPLC fractions of trypsin, Lys-C, and pepsin-derived digest rAsp f 3 peptides were analyzed by MALDI-G-TOF, MALDI-ion trap, and LC/FTICR-MS. FIG. 7 shows an HPLC chromatogram for tryptic rAsp f 3 peptides separated on a reversed phase C18 column, and FIG. 9 shows LC/FTICR-MS/MS spectra of digest rAsp f 3 peptides as identified and assigned by the Global Proteome Machine (GPM) search engine. HPLC fractions were tested for antigenicity using a proliferation assay (FIG. 8), and tested for the presence of antibody-binding epitopes by ELISA. The results of this ELISA assay are summarized in Table 1. "MH$^+$" in Table 1 refers to m/z of the most intense, singly charged and protonated peptide ions observed by MALDI-q-TOF mass spectrometry. "+" refers to detected, "−" refers to non-detected.

| Fraction | IgG1 | IgG2a | MH$^+$ |
|---|---|---|---|
| B6 | − | − | |
| B10 | − | − | |
| B11 | + | + | 1162.56 |
| B12 | + | + | 1162.56 |
| B13 | + | + | 1162.56/1622.89 |
| B14 | − | − | − |
| B15 | + | + | 1622.89 |
| C1 | + | + | 1162.56 |
| C2 | + | + | 1622.89 |
| C3 | + | + | 1162.56/1622.89 |
| C4 | + | + | 1162.56/1622.89 |

Based on these results, a peptide corresponding to residues 54 to 64 of SEQ ID NO:6 (residues 86 to 96 of SEQ ID NO:7) was determined to be a T and B cell epitope, and a peptide corresponding to residues 65 to 77 of SEQ ID NO:6 (residues 97 to 109 of SEQ ID NO:7) was determined to be a B cell epitope.

Figure 10:
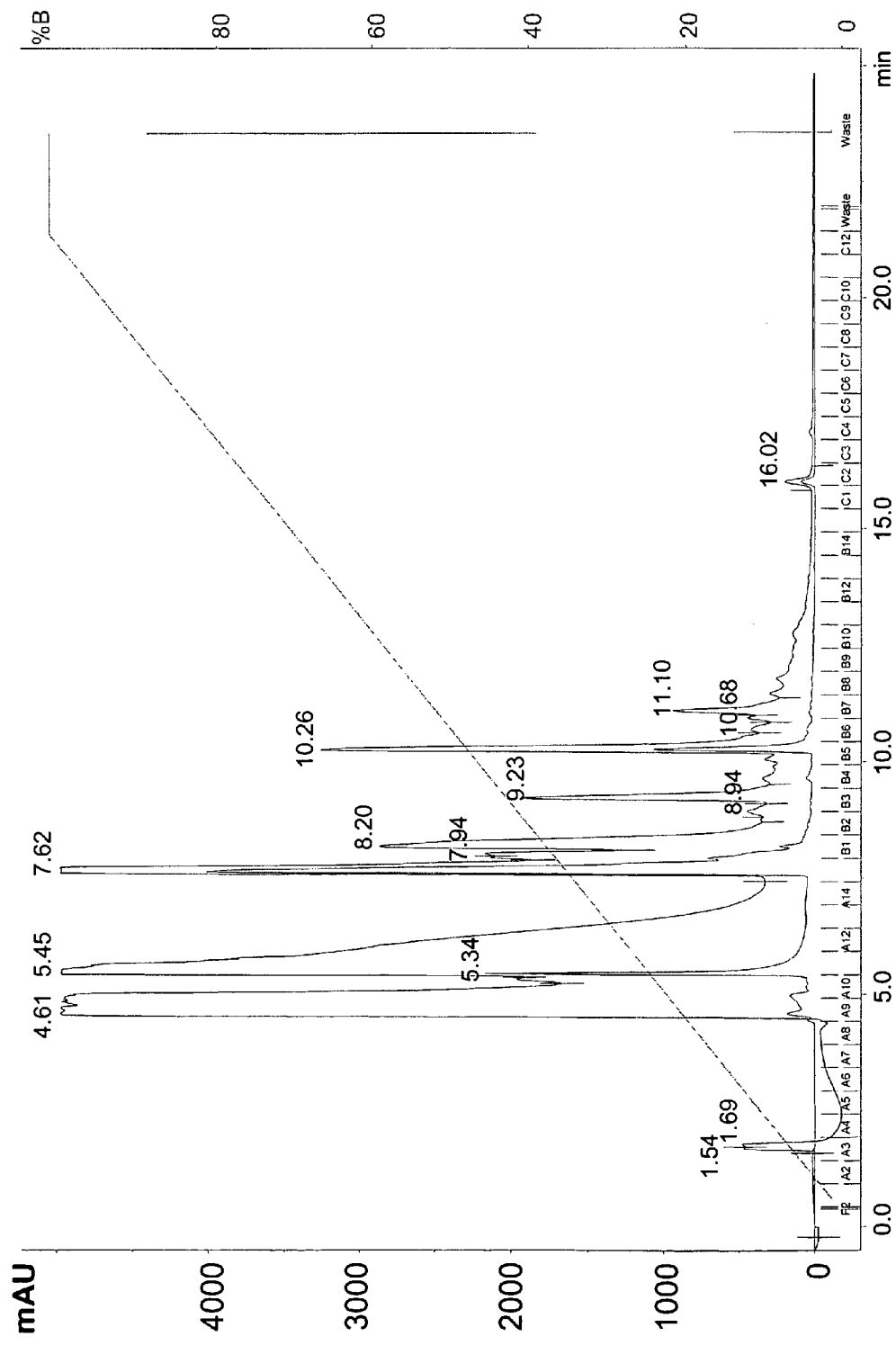
FIG. 10: HPLC chromatogram of trypsin-digested protein extract from *A. fumigatus* hyphae separated on a reversed phase C18 column.
Figure 11A:
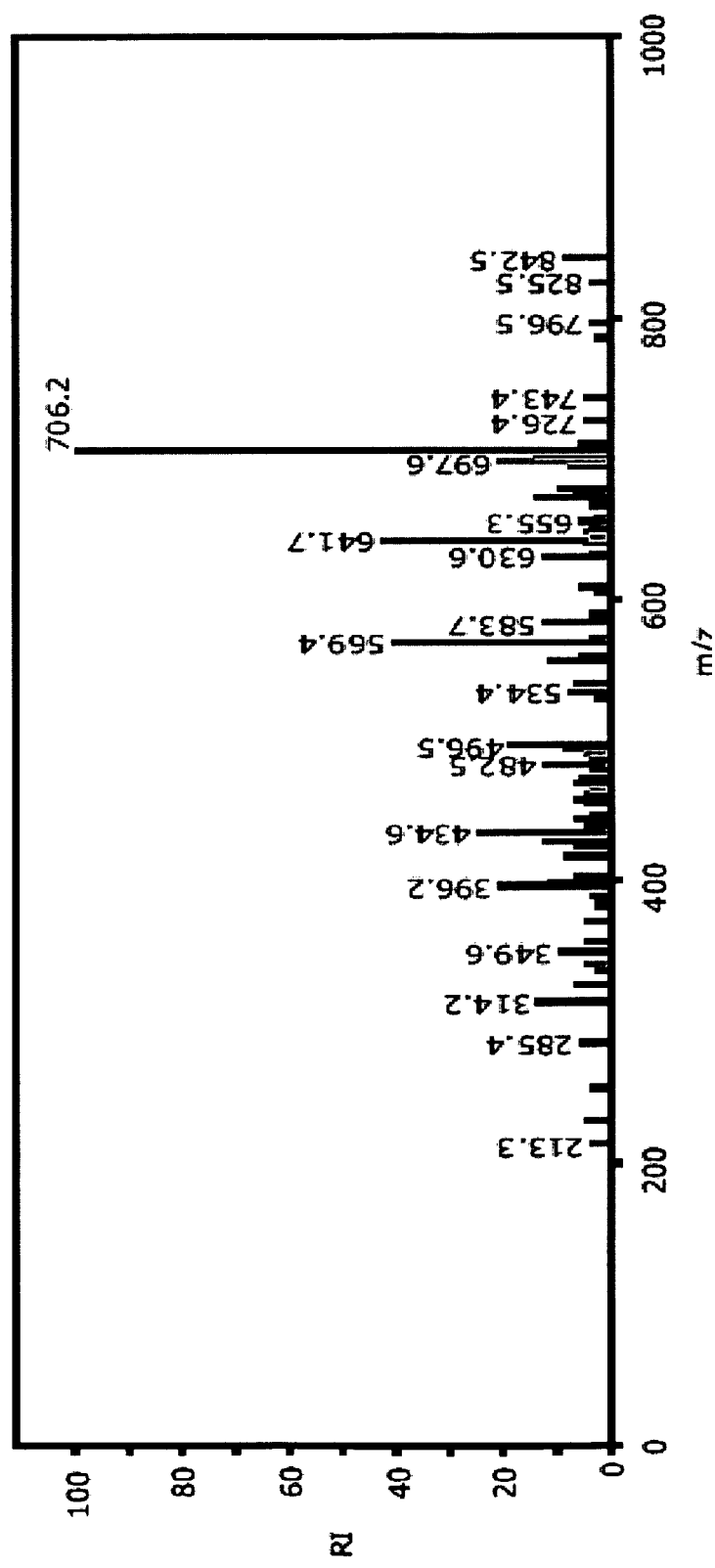
FIG. 11: LC/FTICR-MS/MS spectra of trypsin-digested peptides from *A. fumigatus* hyphal extracts identified and assigned as NAD-dependent formate dehydrogenase using the GPM. A. Peptide B5. B. Peptide B6. C. Peptide B7. D. Peptide B8.
Figure 11B:
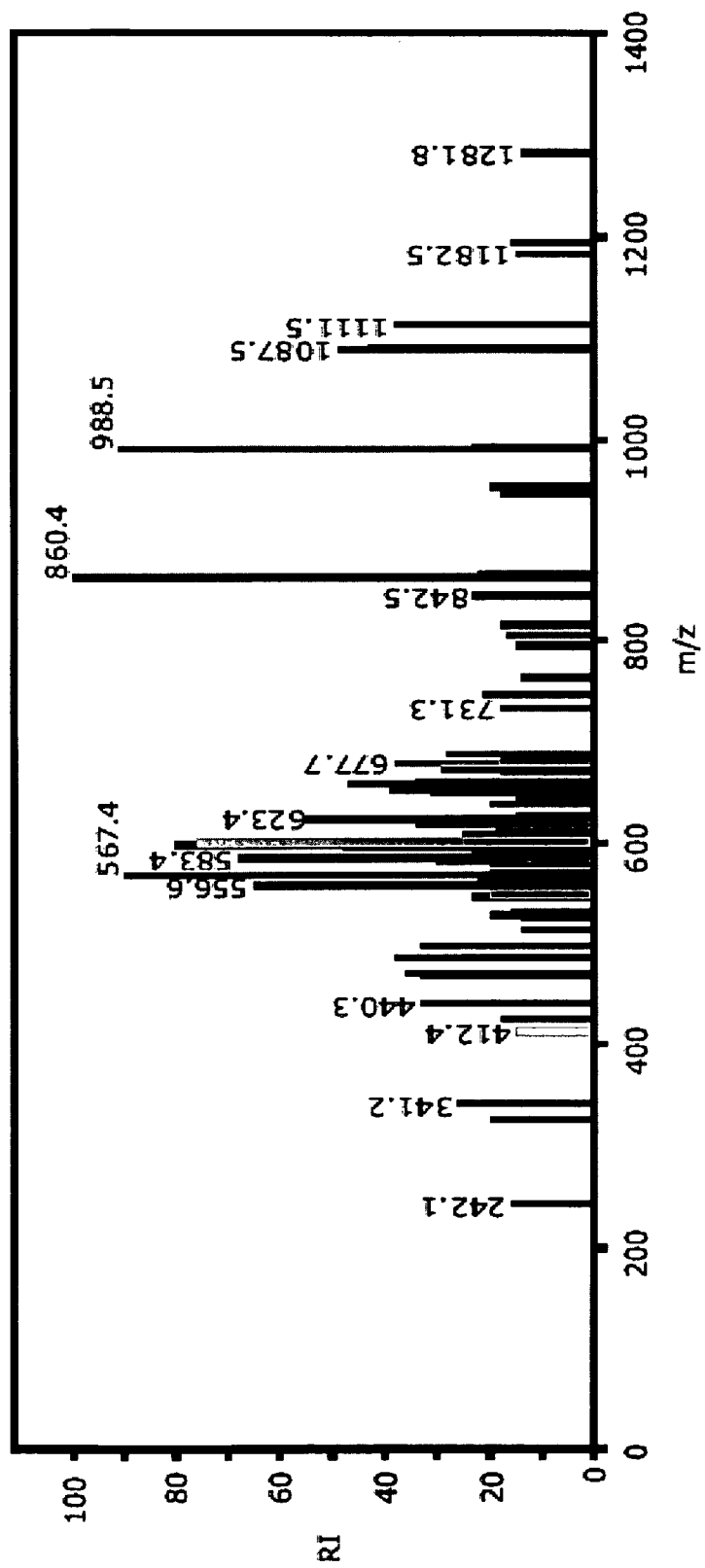
Figure 11C:
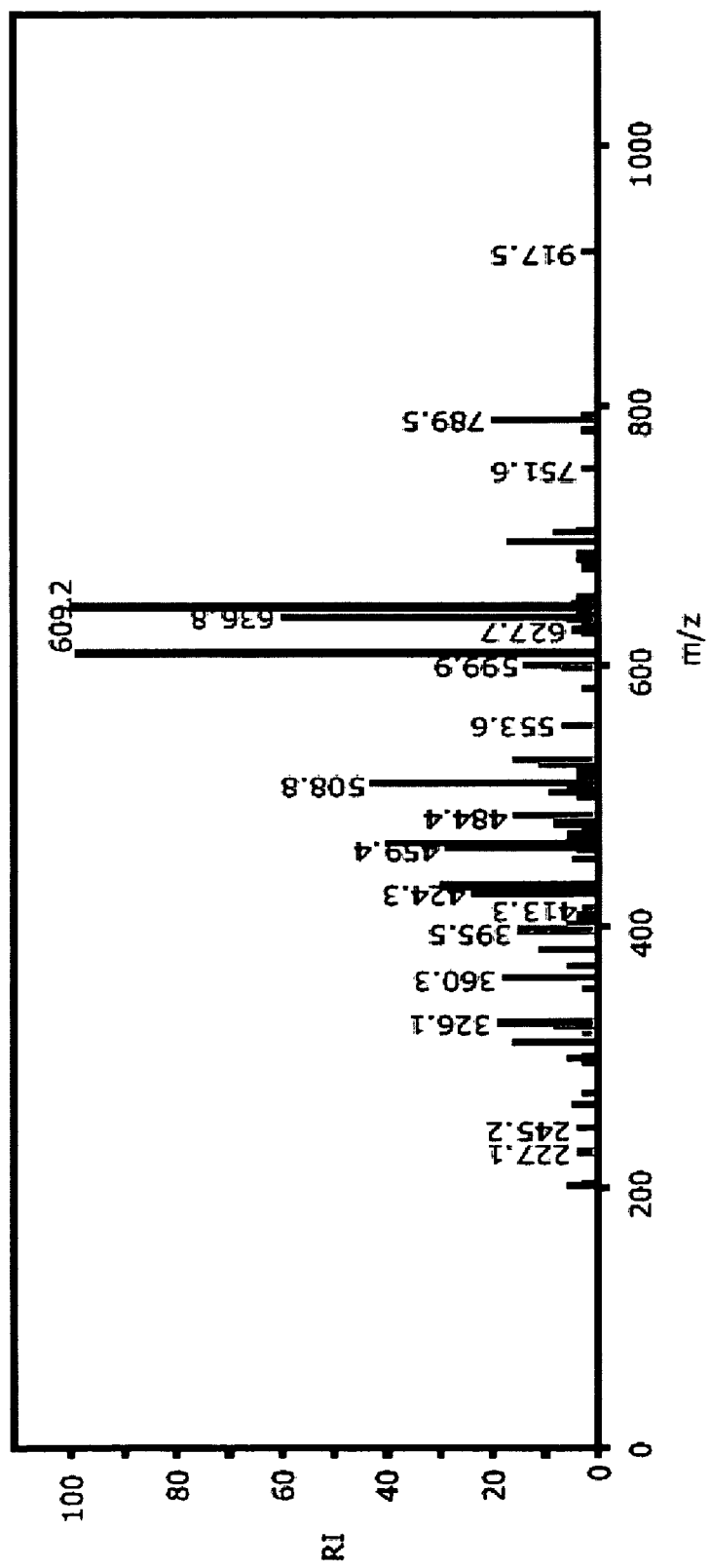
Figure 11D:
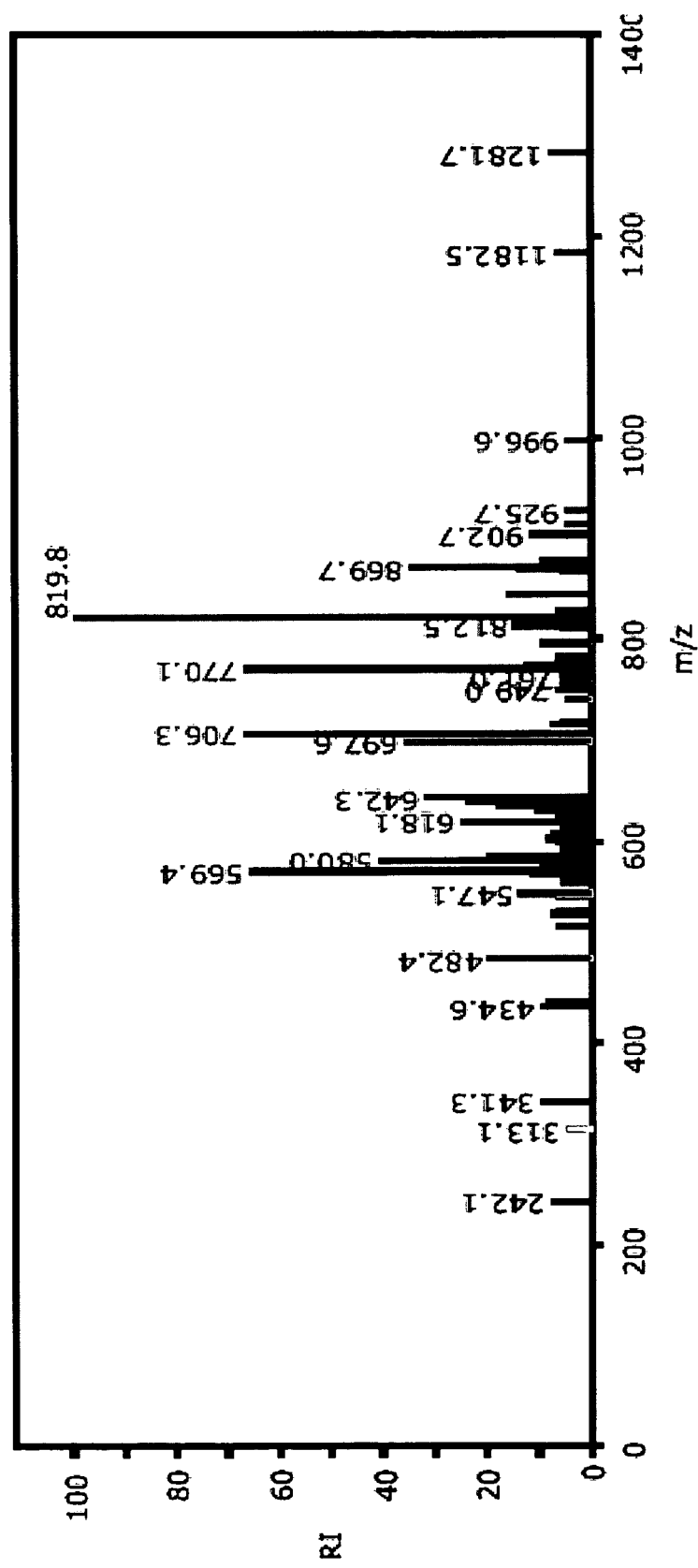
Figure 12:
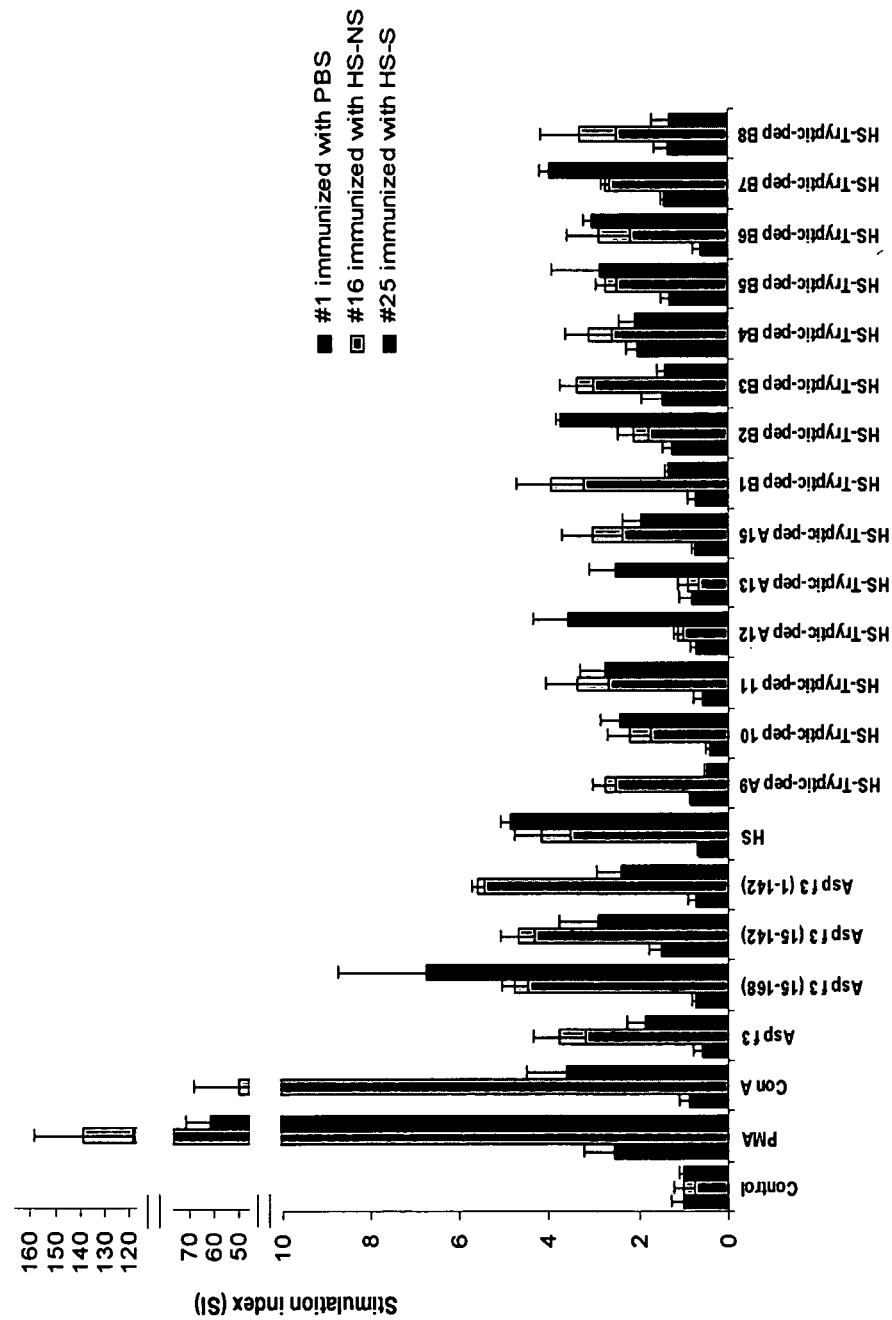
FIG. 12: Lymphoproliferation responses of rAsp f 3-immunized mice to *A. fumigatus* tryptic peptides. Cut-off significance for lymphoproliferation was an SI of 2. Hs=hyphal sonicate; NS=non-sterile; S=sterile.

Similar experiments were conducts to identify T cell epitopes in hyphal protein extracts from *A. fumigatus* (FIGS. 10-12). A peptide having the amino acid sequence set forth in SEQ ID NO:11 was identified as a potential T cell epitope. This peptide was identified and assigned as NAD-dependent formate dehydrogenase using the GPM.

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are expressly incorporated by reference herein in their entirety.

REFERENCES

1. Baddley, W., et al. 2001. Invasive mold infections in allogeneic bone marrow transplant recipients. Clin Infect Dis 32:1319-1324.
2. Bellocchio, S., et al. 2005. Immunity to *Aspergillus fumigatus*: the basis for immunotherapy and vaccination. Med Mycol 43 Suppl 1:S181-S188.
3. Bozza, S., et al. 2002. Vaccination of mice against invasive aspergillosis with recombinant *Aspergillus* proteins and CpG oligodeoxynucleotides as adjuvants. Microbes Infect 4:1281-1290.
4. Bozza, S., et al. 2004. Dendritic cell-based vaccination against opportunistic fungi. Vaccine 22:857-864.
5. Bozza, S., et al. 2003. A dendritic cell vaccine against invasive aspergillosis in allogeneic hematopoietic transplantation. Blood 102:3807-3814.
6. Bradford, M. M. 1976. A rapid and sensitive method for the quantitation of microgram quantities of protein utilizing the principle of protein-dye binding. Analytical Biochemistry 72:248-254.
7. Casadevall, A. and Pirofski, A. 2001. Adjunctive immune therapy for fungal infections. Clin Infect Dis 33:1048-1056.
8. Casadevall, A., and Pirofski, L. A. 2005. Feasibility and prospects for a vaccine to prevent cryptococcosis. Med Mycol 43:667-680.
9. Cenci, E., et al. 2000. T cell vaccination in mice with invasive pulmonary aspergillosis. J Immunol 165:381-388.
10. Denning, D. W. 1998. Invasive aspergillosis. Clin Infect Dis 26:781-803; quiz 804-805.
11. Duthie, R., and D. W. Denning. 1995. *Aspergillus fungemia*: report of two cases and review. Clin Infect Dis 20:598-605.
12. Feldmesser, M. 2005. Prospects of vaccines for invasive aspergillosis. Med Mycol 43:571-87.
13. Galagan, J. E., et al. 2005. Sequencing of *Aspergillus nidulans* and comparative analysis with *A. fumigatus* and *A. oryzae*. Nature 438:1105-1115.
14. Garrard, L. J., and J. M. Goodman. 1989. Two genes encode the major membrane-associated protein of methanol-induced peroxisomes from *Candida boidinii*. Journal of Biological Chemistry 264:13929-13937.
15. Gupta, A. K., and E. Tomas. 2003. New antifungal agents. Dermatol Clin 21:565-576.
16. Hamza, N. S., Ghannoum, M. A., Lazarus, H. M. 2004. Choices aplenty: antifungal prophylaxis in hematopoietic stem cell transplant recipients. Bone Marrow Transplant 34:377-389.
17. Hemmann, S., Blaser, K., Crameri, R. 1997. Allergens of *Aspergillus fumigatus* and *Candida boidinii* share IgE-binding epitopes. Am J Respir Crit. Care Med 156:1956-1962.
18. Herbrecht, R., et al. 2002. Voriconazole versus amphotericin B for primary therapy of invasive aspergillosis [see comment]. New England Journal of Medicine 347:408-415.
19. Ho, P. L., and Yuen, K. Y. 2000. Aspergillosis in bone marrow transplant recipients. Crit. Rev Oncol Hematol 34:55-69.
20. Huang, C. F., et al. 2006. The immune response induced by hepatitis B virus principal antigens. Cell Mol Immunol 3:97-106.
21. Ito, J. I., and J. M. Lyons. 2002. Vaccination of corticosteroid immunosuppressed mice against invasive pulmonary aspergillosis. J Infect Dis 186:869-871.
22. Kalkum, M., Lyon, G. J., Chait, B. T. 2003. Detection of secreted peptides by using hypothesis-driven multistage mass spectrometry. Proc Natl Acad Sci USA 100:2795-2800.
23. Kibbler, C. 2003. *Aspergillus*: the invisible threat. Nurs Times 99:48-50.

24. Kodzius, R., et al. 2003. Rapid identification of allergen-encoding cDNA clones by phage display and high-density arrays. Comb Chem High Throughput Screen 6:147-154.
25. Krutchinsky, A. N., Kalkum, M., Chait, B. T. 2001. Automatic identification of proteins with a MALDI-quadrupole ion trap mass spectrometer. Anal Chem 73:5066-5077.
26. Kurup, V. P., et al. 2001. Purified recombinant *A. fumigatus* allergens induce different responses in mice. Clin Immunol 98:327-336.
27. Latge, J. P. 1999. Antigen and DNA patterns characteristic of *Aspergillus fumigatus*. Contrib Microbiol 2:69-87.
28. Latge, J. P. 1999. *Aspergillus fumigatus* and aspergillosis. Clin Microbiol Rev 12:310-350.
29. Li, S. W., et al. 2005. A bacterially expressed particulate hepatitis E vaccine: antigenicity, immunogenicity and protectivity on primates. Vaccine 23:2893-2901.
30. Lin, J. et al. 2001. Aspergillosis case-fatality rate: systematic review of the literature. Clin Infect Dis 32:358-66.
31. Liu, Q., et al. 1999. The binding interface between an E2 (UBC9) and a ubiquitin homologue (UBL1). J Biol Chem 274:16979-16987.
32. Machida, M., et al. 2005. Genome sequencing and analysis of *Aspergillus oryzae*. Nature 438:1157-1161.
33. Maschke, M., et al. 1999. Opportunistic CNS infection after bone marrow transplantation. Bone Marrow Transplant 23:1167-1176.
34. Montagnoli, C., et al. 2003. A role for antibodies in the generation of memory antifungal immunity. Eur J Immunol 33:1193-1204.
35. Nierman, W. C., et al. 2005. Genomic sequence of the pathogenic and allergenic filamentous fungus *Aspergillus fumigatus*. Nature 438:1151-1156.
36. Pizza, M., et al. 2000. Identification of vaccine candidates against serogroup B meningococcus by whole-genome sequencing. Science 287:1816-20.
37. Ramachandran, H., et al. 2002. IgE binding conformational epitopes of Asp f 3, a major allergen of *Aspergillus fumigatus*. Clin Immunol 103:324-333.
38. Rappuoli, R., and Covacci, A. 2003. Reverse vaccinology and genomics. Science 302:602.
39. Rementeria, A., et al. 2005. Genes and molecules involved in *Aspergillus fumigatus* virulence. Rev Iberoam Micol 22:1-23.
40. Roilides, E. et al. 1993a. Prevention of corticosteroid-induced suppression of human polymorphonuclear leukocyte-induced damage of *Aspergillus fumigatus* hyphae by granulocyte colony-stimulating factor and gamma interferon. Infect Immun 61:4870-4877.
41. Roilides, E., et al. 1993b. Prevention of corticosteroid-induced suppression of human polymorphonuclear leukocyte-induced damage of *Aspergillus fumigatus* hyphae by granulocyte colony-stimulating factor and gamma interferon. Infect Immun 61:4870-4877.
42. Sambrook, J., and Russell, D. W. 2001. Molecular cloning: a laboratory manual, 3rd ed., Cold Spring Harbor Laboratory Press, Cold Spring Harbor, N.Y.
43. Schaffner, A., Douglas, H., and Braude, A. 1982. Selective protection against conidia by mononuclear and against mycelia by polymorphonuclear phagocytes in resistance to *Aspergillus*. Observations on these two lines of defense in vivo and in vitro with human and mouse phagocytes. J Clin Invest 69:617-631.
44. Schaffner, A., et al. 1985. Therapeutic concentrations of glucocorticoids suppress the antimicrobial activity of human macrophages without impairing their responsiveness to gamma interferon. J Clin Invest 76:1755-1764.
45. Stevens, D. A. 2004. Vaccinate against aspergillosis! A call to arms of the immune system. Clin Infect Dis 38:1131-1136.
46. Subira, M., et al. 2002. Invasive pulmonary aspergillosis in patients with hematologic malignancies: survival and prognostic factors. Haematologica 87:528-534.
47. Weig, M., et al. 2001. Use of recombinant mitogillin for improved serodiagnosis of *Aspergillus fumigatus*-associated diseases. J Clin Microbiol 39:1721-1730.
48. Wiederhold, N. P., Lewis, R. E., and Kontoyiannis, D. P. 2003. Invasive aspergillosis in patients with hematologic malignancies. Pharmacotherapy 23:1592-1610.

What is claimed is:

1. A composition comprising an effective immunizing amount of a truncated form of an isolated *Aspergillus fumigatus* protein Asp f 3 and an adjuvant, wherein said truncated form of Asp f 3 consists of residues 15-142 of SEQ ID NO:6.

* * * * *